US007630908B1

(12) United States Patent
Amrien et al.

(10) Patent No.: US 7,630,908 B1
(45) Date of Patent: Dec. 8, 2009

(54) WIRELESS ELECTRONIC PRESCRIPTION SCANNING AND MANAGEMENT SYSTEM

(76) Inventors: John Amrien, 4 Bypass Rd., Suite 201, Salem, NJ (US) 08079; Paul Amrien, 5990 Naples Plz., #4, Long Beach, CA (US) 90803; Martin Smith, 250 62nd St., Newport Beach, CA (US) 92663; Pine Blossom Harvey, 250 62nd St., Newport Beach, CA (US) 92663

( * ) Notice: Subject to any disclaimer, the term of this patent is extended or adjusted under 35 U.S.C. 154(b) by 0 days.

(21) Appl. No.: 09/562,386

(22) Filed: May 1, 2000

(51) Int. Cl.
*G06F 19/00* (2006.01)
*G06Q 50/00* (2006.01)
*G06K 19/00* (2006.01)

(52) U.S. Cl. .............................. 705/3; 705/2; 235/487

(58) Field of Classification Search .................. 705/2–3
See application file for complete search history.

(56) References Cited

U.S. PATENT DOCUMENTS 5,315,505 A * 5/1994 Pratt et al. .................. 600/300

(Continued)

FOREIGN PATENT DOCUMENTS

WO    WO 97/17671    5/1997

(Continued)

OTHER PUBLICATIONS

Donald, J. B. "Prescribing costs when computers are used to issue all prescriptions." Jul. 1, 1989; British Medical Journal. ; vol. 299 (No. 6690): pp. 28-30.*

(Continued)

*Primary Examiner*—C. Luke Gilligan
*Assistant Examiner*—Rachel L Porter
(74) *Attorney, Agent, or Firm*—Choate, Hall & Stewart LLP; Brenda Herschbach Jarrell

(57) ABSTRACT

Methods and systems for rapidly and conveniently creating prescriptions through the use of portable digital assistants (PDAs) and bar code scanning technology are provided. Prescriptions are created using a form-based approach in which prescribing options are presented to the prescriber for selection. The system allows entry of medication and patient ID by scanning bar codes. A bar code is generated for each prescription and is used to access the prescription information in a database. The bar code and prescription information can be printed on a ticket, which can be presented at a pharmacy when the prescription is picked up. The use of bar codes allows several levels of checking to ensure that the correct medication is dispensed and that the prescription is valid. Prescription information is transmitted between prescribers and pharmacies via a central site at which prescription information is stored. In a preferred embodiment of the invention communication occurs over the Internet, and the creation and transmission of prescriptions are coordinated by a World Wide Web service which sends Web pages to PDAs to present and gather prescription information. The Web pages can provide links to patient and medication information, and the system can advise the prescriber if there is a contraindication to the medication about to be prescribed. The Web service transmits prescription information to pharmacies, receives notification when prescriptions are fulfilled, and can perform other functions such as notifying patients or physicians when prescriptions are close to running out. The Web service can further be used to keep track of medication sample package inventories at prescribing locations such as physician offices. Prescription data can be used to perform market research in a timely fashion.

16 Claims, 22 Drawing Sheets

U.S. PATENT DOCUMENTS

| | | | | |
|---|---|---|---|---|
| 5,451,760 A | * | 9/1995 | Renvall | 235/375 |
| 5,542,420 A | * | 8/1996 | Goldman et al. | 600/301 |
| 5,597,995 A | | 1/1997 | Williams et al. | 235/375 |
| 5,628,530 A | | 5/1997 | Thornton | 283/67 |
| 5,654,534 A | | 8/1997 | Coleman | 235/472 |
| 5,654,543 A | | 8/1997 | Li | 250/287 |
| 5,671,282 A | * | 9/1997 | Wolff et al. | 713/179 |
| 5,737,539 A | * | 4/1998 | Edelson et al. | 705/3 |
| 5,758,095 A | | 5/1998 | Albaum et al. | 395/202 |
| 5,832,449 A | | 11/1998 | Cunningham | 705/3 |
| 5,845,255 A | * | 12/1998 | Mayaud | 705/3 |
| 5,845,264 A | | 12/1998 | Nellhaus | 705/28 |
| 5,883,370 A | | 3/1999 | Walker et al. | 235/375 |
| 5,884,273 A | | 3/1999 | Sattizahn et al. | 705/3 |
| 6,347,329 B1 | * | 2/2002 | Evans | 709/202 |
| 6,408,330 B1 | * | 6/2002 | DeLaHuerga | 709/217 |

FOREIGN PATENT DOCUMENTS

| | | |
|---|---|---|
| WO | WO 98/28676 | 7/1998 |
| WO | WO 98/39720 | 9/1998 |
| WO | WO 99/10829 | 3/1999 |

OTHER PUBLICATIONS

MacArthur Fellowships: 3 doctors awarded grants, *American Medical News*, available at http://www.ama-assn.org/amednews/2006/10/16/prsb1016.htm., Oct. 16, 2006.

* cited by examiner

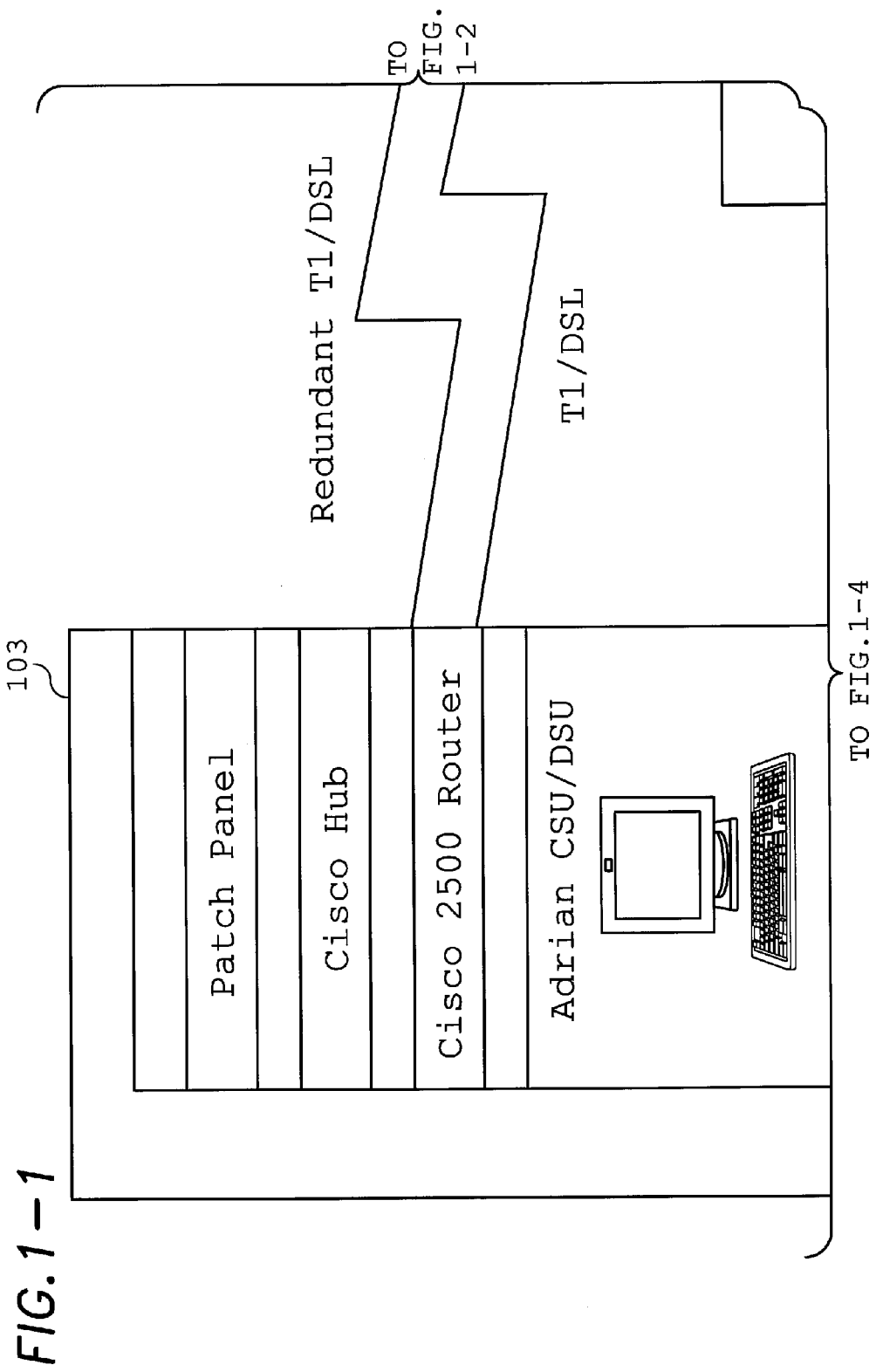

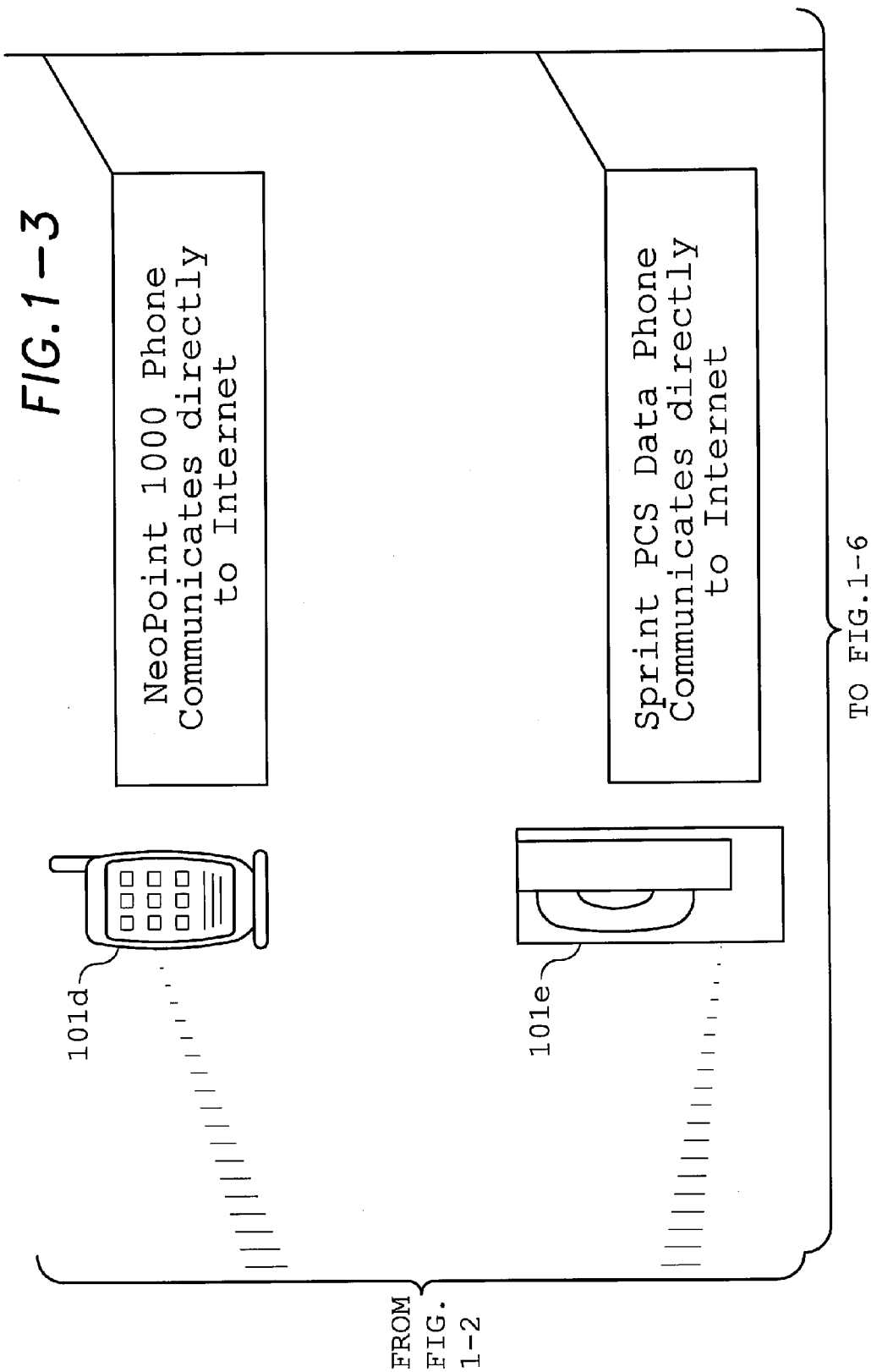

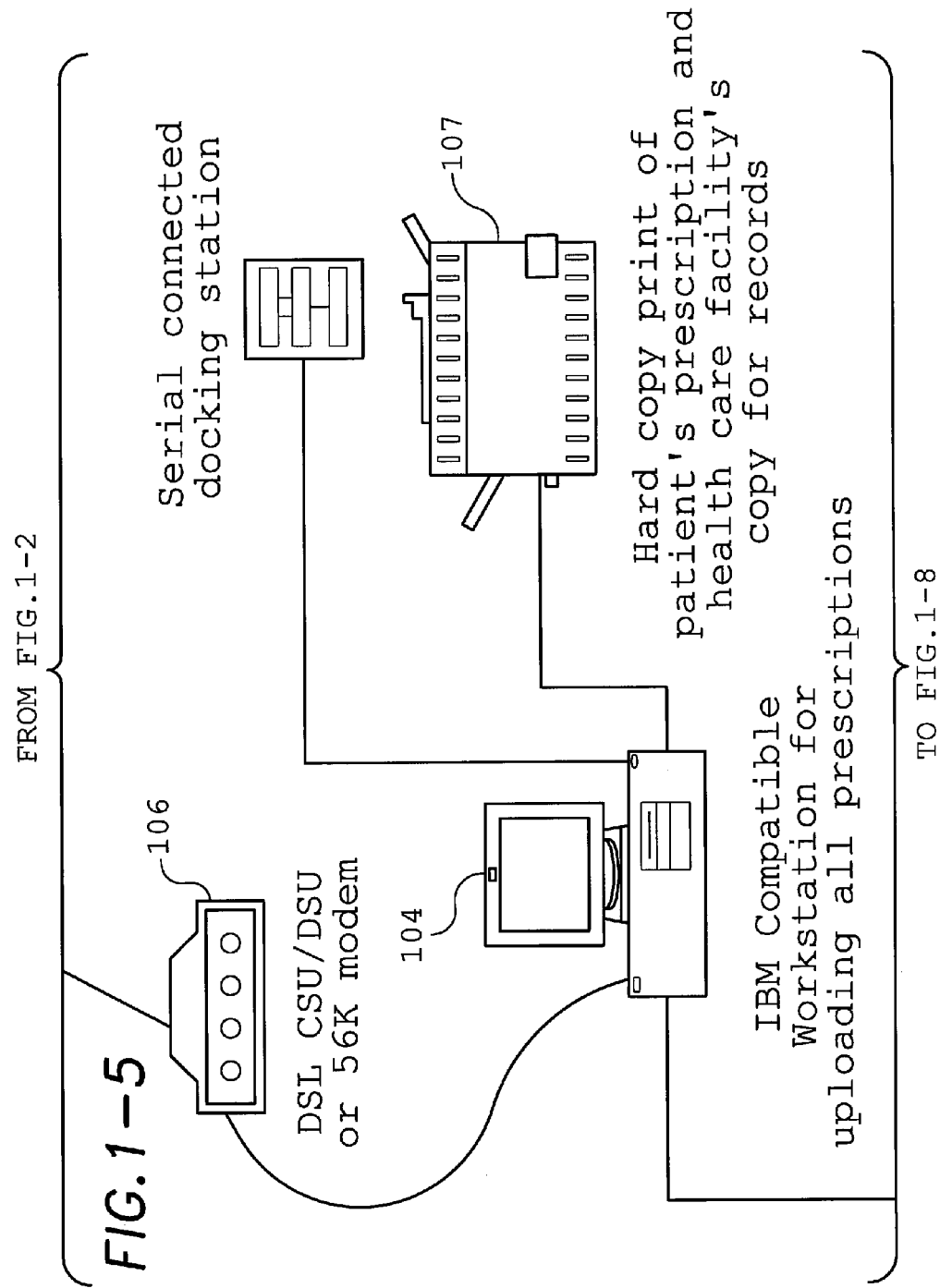

Cassiopeia, Currently connects via docking cradle to upload all prescriptions to in house Internet connected PC, but will eventually use wireless ethernet compact flash FROM FIG.1-6
*FIG.1-9*
Palm VII, communicates with wireless ethernet technology in the office.
Symbol 2700 communicates with wireless ethernet technology in the office. This unit has Integrated bar code reader
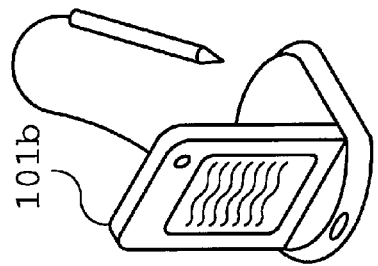
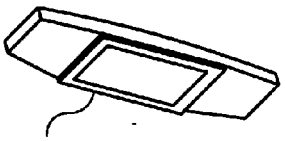
FROM FIG. 1-8

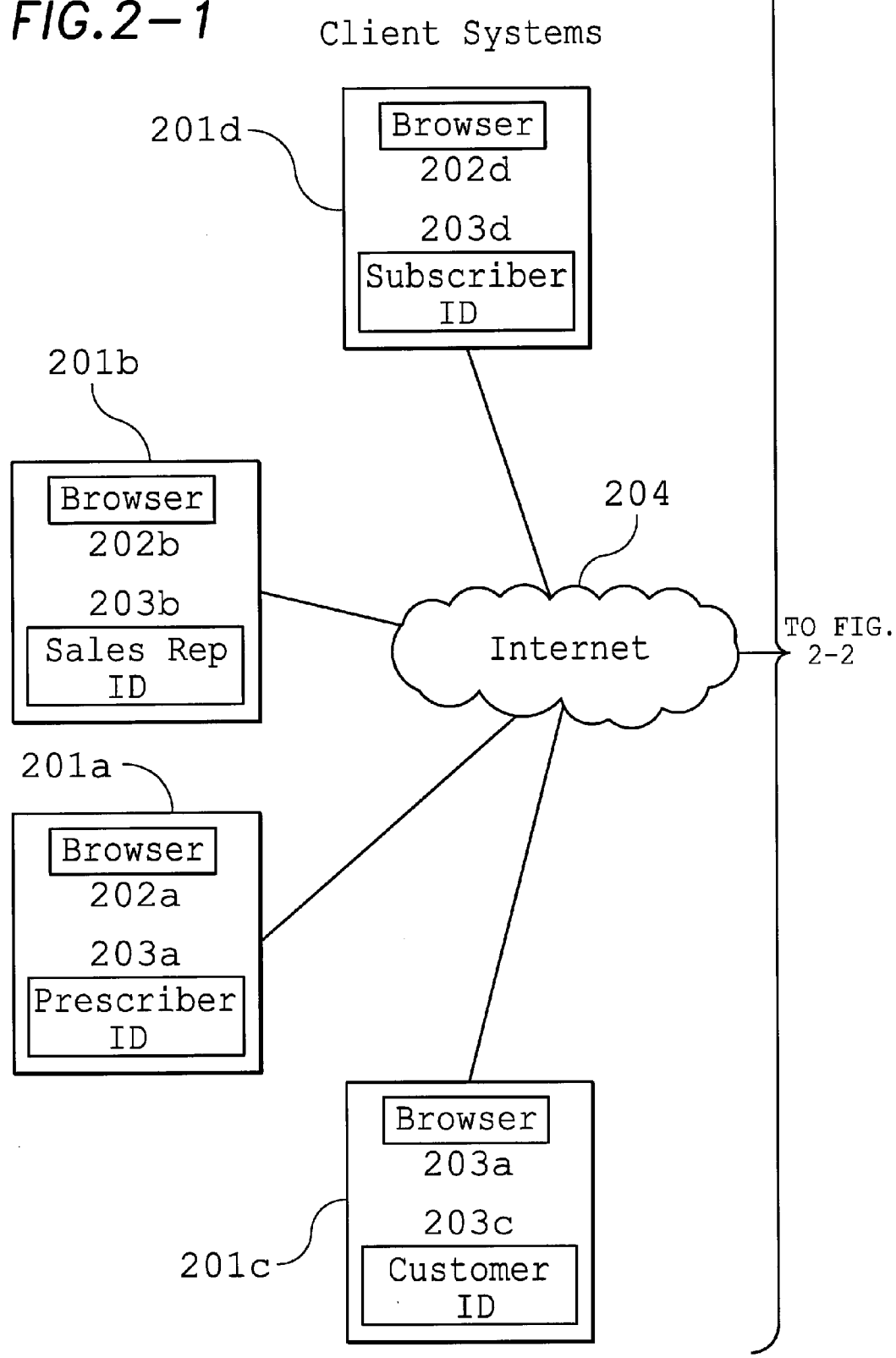

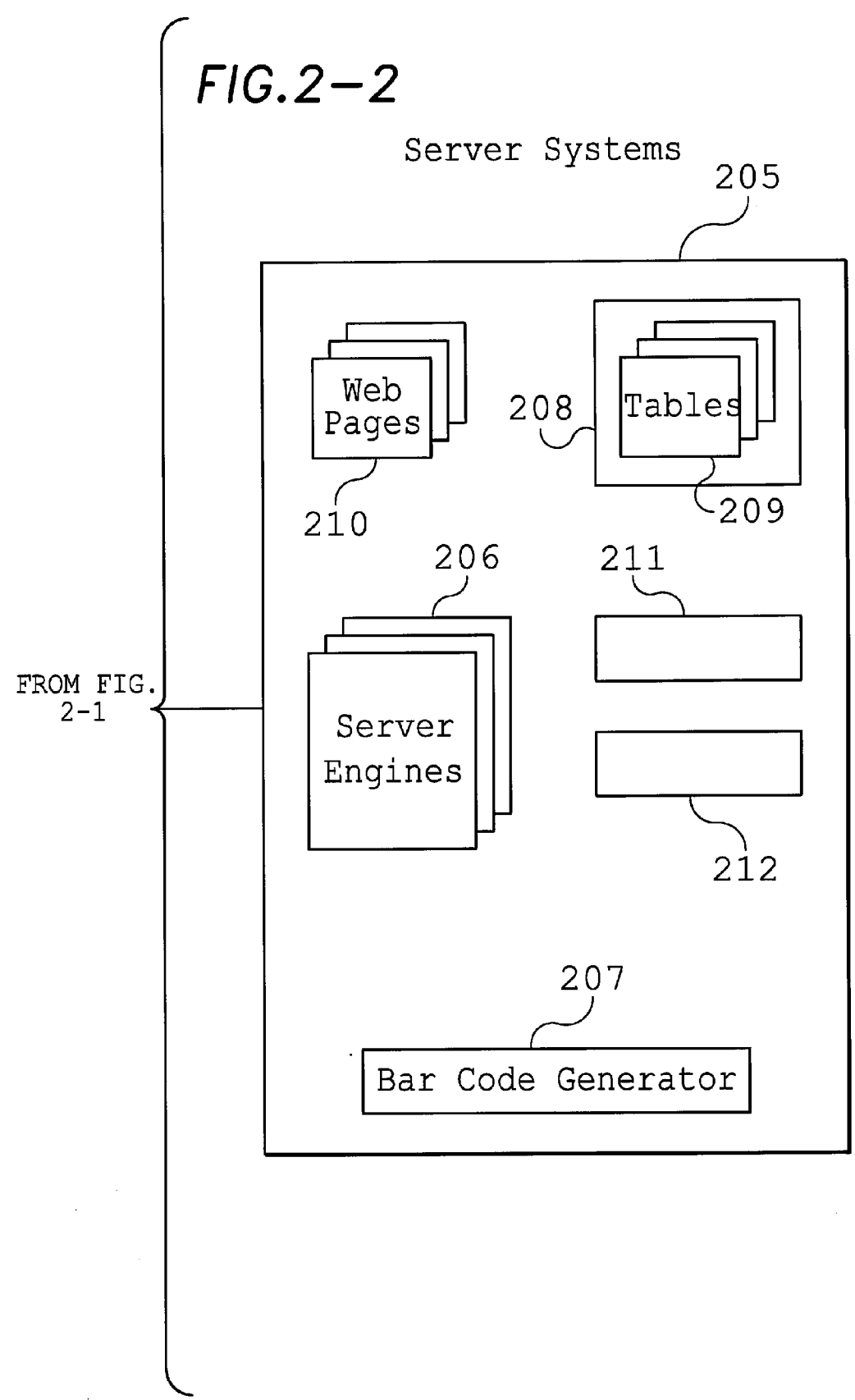

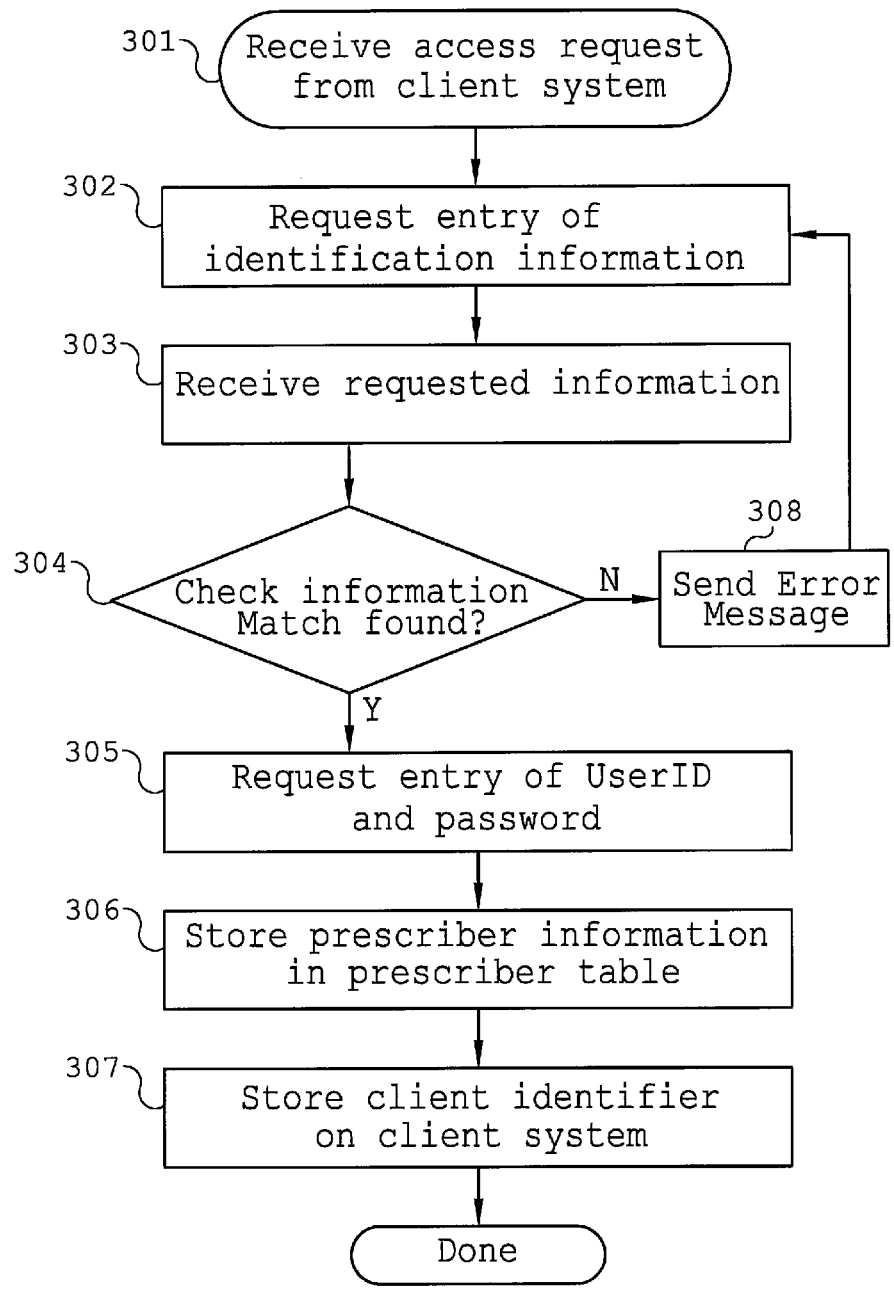

TO FIG. 4-2

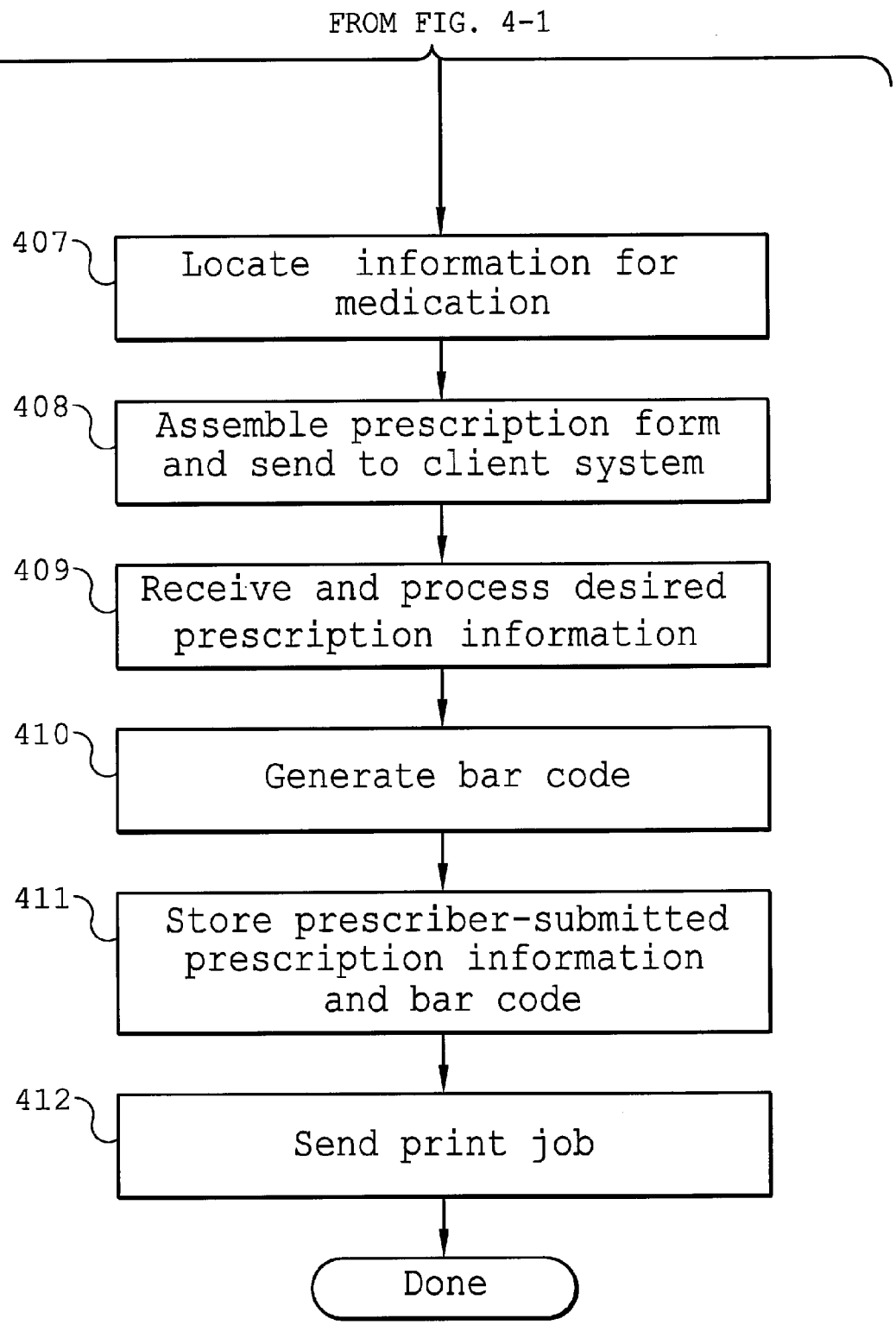

FIG.8

Prescription

Patient:
Mr. Bill Clinton
Medication:
Zestril

[ 10 mg ▼ ]  [ bid ▼ ]  [ PO ▼ ]

\# to dispense      Refills
[ 100 ▼ ]          [ 3 ▼ ]

[✓] Do Not Substitute

Signature

[ Submit ]

FROM FIG.9-1

10 mg    bid    PO to dispense    Refills
100    3

☑ Do Not Substitute

Signature:

Submit    Cancel

WIRELESS ELECTRONIC PRESCRIPTION SCANNING AND MANAGEMENT SYSTEM

BACKGROUND OF THE INVENTION

In most areas of modern medical practice a typical physician is likely to prescribe a variety of medications on a daily basis. Unlike many areas of medicine, for example medical imaging, that have incorporated sophisticated computer technology with resulting improvements in patient care, the issuing of prescriptions has remained primarily a manual task. Yet issuing prescriptions is one of the most important and ubiquitous tasks of the physician. It is estimated that over two thirds of all physician-patient encounters culminate with the writing of a prescription.

After obtaining relevant historical information from a patient, performing a physical examination along with appropriate laboratory tests and possibly consulting the patient's medical record, the physician arrives at a diagnosis or at least an evaluation of the patient's condition. Following this process the physician typically selects one or more medications with the goal of treating the patient's condition and/or relieving symptoms. In making the selection, the physician utilizes patient-specific information including past medical history, current condition and concurrent medications, possible contraindications and potential drug interactions. The physician also relies on his or her preferences based on past experience with various medications and also on new information such as that provided by drug industry representatives and recent scientific research.

In addition to choosing the medication, the physician must also select a dosage amount, dosing time, and route of administration. The physician must sign the prescription and provide his/her license number, thereby confirming that the prescription was written by an authorized prescriber. The process of writing prescriptions varies somewhat depending upon the clinical setting. For example, in hospitals an order to administer a drug may be written directly in a patient's chart or entered into a computerized, hospital-based medical order system. The order is transmitted to the hospital pharmacy either directly or by a nurse, and the medication is administered to the patient by a nurse.

Far more typically prescriptions are written in an outpatient setting. The information that the physician must include on the prescription includes patient identification, medication name, dosage amount, timing, total amount of medication to be given to the patient, information regarding refills, physician's signature and license number, date, and possibly brief instructions and/or warnings. Optionally the physician can indicate that a brand name medication is to be dispensed as written, i.e., that the pharmacist should not substitute a generic medication. In the absence of such an indication the pharmacist is free to substitute a generic medication for a branded drug. Prescription information is typically written on a small piece of paper which may be preprinted with the physician's name and/or place of work. The patient presents the written prescription to a pharmacy for fulfillment. The pharmacist then fills the prescription, generating a label listing the name of the drug along with instructions to the patient regarding when to take the medication and how much to take each time.

The writing and transmission of prescriptions in a timely and accurate manner is of the utmost importance. Unfortunately, the system as described above has significant shortcomings. Firstly, it relies upon the handwriting of physicians, which is notoriously poor. If a pharmacist is unable to correctly interpret the medication name, dosage information, etc. written by the physician, there is a chance that the wrong medication will be given to the patient. To prevent such mishaps pharmacists frequently must contact the physician by phone to confirm the necessary information. It has been estimated that as many as ten percent of written prescriptions result in such "callbacks", representing a waste of physician and pharmacist time and introducing an opportunity for error if the physician cannot accurately recall exactly what he or she originally wrote. Callbacks also result in patient inconvenience and delay in obtaining necessary medication. Another drawback of the current system is the opportunity for fraudulent prescribing. In many health care settings there are few safeguards on the availability of "official-looking" prescription pads, and it is relatively easy for unauthorized persons to obtain them and write prescriptions, as long as these persons are able to learn a physician's license number. Pharmacists typically have no means of verifying that the signature on a prescription indeed belongs to an authorized prescriber. Furthermore, pharmacists have no way of verifying that the prescription information has not been altered, e.g., by changing the number of pills to be dispensed. There exists a need for methods and systems that will reduce or eliminate problems associated with inability to read physician handwriting on prescriptions. There further exists a need to minimize opportunities for fraud associated with prescription filling.

Computer-based systems for entering prescriptions can provide a number of advantages including minimizing problems with physician handwriting and potential fraud. In today's time and cost conscious environment, computer-based prescription and management can also offer significant improvements in efficiency. Furthermore, if connected to databases containing patient records, they can alert the physician if the patient has previously experienced an allergic reaction to a particular medication or has a contraindication to that medication. If connected to databases containing drug information, they can alert the physician to possible drug interactions and contraindications. It is recognized that a significant number of adverse patient experiences result from avoidable medication errors. Accordingly, there exists a need for improved methods and systems for checking that medications are prescribed appropriately.

Despite the advantages mentioned above, there are several barriers to the adoption of computer-based prescription entry. Physicians are highly mobile, often engaged in professional activities at multiple geographically distinct locations. They are frequently involved in patient encounters in sites such as examination rooms, hospital rooms, specialist areas such as imaging suites, etc., where they may not have access to a computer terminal. Small notebook computers, which a physician could transport, would theoretically eliminate the problem of limited access to terminals. However, given that physicians frequently already carry about diagnostic equipment, pocket references, etc., it is unlikely that they would embrace the notion of adding a notebook computer to their burden. Furthermore, such computers must often be plugged into wall jacks in order to electronically transmit information over a computer network. In addition, physicians are increasingly being consulted about patients over telecommunications equipment such as cellular phones and in settings in which use of either a traditional or notebook computer is impractical.

In order for a computer-based system to be widely adopted it must rival the current format of the written prescription in terms of rapidity and ease of use. At present, a physician can write a prescription by hand literally within seconds, at any time or place. Prescriptions are typically written at the termination of a patient encounter. With the increasing pressure on physicians to see more and more patients, it is typical for the end of the encounter to be very rushed, particularly if the physician feels that he or she has fallen behind the planned schedule. Most experienced physicians have long since memorized names, doses, etc., for medications that they prescribe frequently. Physicians will not be willing to adopt a system that requires a time-consuming selection process or that constrains them to enter information other than that necessary for appropriate completion of the prescription. They will not be willing to scroll through long lists of drugs, doses, and formulation options, or to laboriously enter drug names on a miniature keyboard. Thus despite the advantages of computer based prescription entry, it has not been widely adopted, particularly in outpatient settings and independent private practices. There exists a need for a streamlined, user-friendly electronic prescription entry system that will offer convenience that rivals or exceeds the traditional handwritten prescription in terms of ease of use for the prescriber.

Although prescriptions are generally written by physicians and filled by pharmacists, both providers and the patient population rely upon the activities of pharmaceutical manufacturers to ensure that medications will be available for dispensing. In a broader sense, the health care community and the population as a whole rely upon pharmaceutical companies to develop and introduce new and effective medications and to appropriately inform both groups as to the availability and advantages of these new medications. Through scientific publications, advertising both to the medical community and increasingly to the public, and through the distribution of free drug samples to physicians, pharmaceutical companies provide relevant and timely information about their products.

It is common practice for pharmaceutical sales representatives to distribute free drug samples to physicians, who in turn can give them to their patients. Distribution of free samples serves a number of important roles. The presence of these samples alerts the physician to the availability of a new drug, encouraging him to consider whether it might offer an improvement over the treatments he is currently prescribing. Patients can take the drug on a trial basis without needing to purchase it, thus avoiding the possibility that a patient will end up paying for a drug that is not effective for his condition. Physicians can gain experience with the medication, which may lead them to recommend its addition to hospital formularies.

Currently most distribution of free samples is done when a sales representative visits a physician, typically at the location of his practice. The representative gives the physician a certain number of free samples and typically writes down the number of samples of each medication distributed. Much like a physician, sales representatives are highly mobile and rely on the convenience of a traditional pen/pencil based system to record their transactions rather than using a desktop or notebook computer. To work properly, however, the present system requires that the sales representative manually maintains organized, up-to-date records of when and where he distributed sample and what lot numbers he distributed to a particular physician or site. In addition, the current system does not provide any means by which a sales representative can determine how much of the material distributed has been used. Thus physicians may run out of samples before the next time the representative visits. There exists a need for an improved system by which sales representatives and pharmaceutical manufacturers can record and track sample distribution and usage.

To operate effectively in today's competitive marketplace and to respond rapidly to new opportunities and demands, pharmaceutical companies need to be able to track the number of prescriptions written for the medications they produce. Present means to obtain this type of data rely on retrospective surveys and often result in incomplete data available only months after the relevant prescribing activity has taken place. Thus there exists a need for a system whereby pharmaceutical manufacturers can obtain timely information regarding the usage of their products.

SUMMARY OF THE INVENTION

In one aspect, the present invention provides methods and systems for rapidly and conveniently creating prescriptions through the use of client and server systems and bar code scanning technology. In particular, client systems of the invention include portable digital assistants (PDAs). The invention further provides methods for electronically sending prescription information between client systems operated by prescribers and client systems at pharmacies via a server system at a central site where prescription information is stored. In a preferred embodiment of the invention communication occurs over the Internet, and the creation and sending of prescriptions are coordinated by a World Wide Web service. In a preferred embodiment of the invention patient name and medication name are entered into the PDA by scanning bar codes. Other prescription information is entered by the physician using a set of forms containing information such as appropriate dosage and route of administration. In a preferred embodiment of the invention the forms are provided as Web pages.

After all prescription information has been entered by a prescriber the information is sent to a Web service including a server engine, a bar code generator, and a database containing prescriber information, prescription information, generated prescriptions, and additional information. In a preferred embodiment of the invention, a bar code and corresponding bar code reference number are generated for each prescription. The reference number is stored in the prescription information record and serves as the key into the database to uniquely identify the record with which it is associated. The reference number is used to access the prescription information, thus providing a single identifier by which the prescription information can be viewed, checked, updated, or analyzed by individuals who are authorized to do so.

In a preferred embodiment of the invention the prescription information, including the bar code, is printed by a printer located at an appropriate site so that the patient can obtain a paper copy of the prescription. In addition, the Web service sends the prescription information along with the bar code to a pharmacy, which can be preselected either at the time of prescription creation or at a later time. In a preferred embodiment of the invention the patient presents the ticket when picking up the prescription, and the pharmacist accesses the Web service, scans in the prescription bar code, and checks the prescription information against the prescription information stored in the database. In preferred embodiments of the invention various checking steps are performed to confirm the prescription and ensure that the correct medication is dispensed. In a preferred embodiment of the invention the pharmacist notifies the server engine that the prescription has been filled, and the server engine updates the prescription database accordingly. In preferred embodiments of the invention the server engine performs additional functions such as notifying the prescriber if the patient fails to fill a prescription, notifying the patient before the prescription runs out, etc.

In another aspect, the invention provides methods and systems for ensuring that a physician selection of a nongeneric drug when creating a prescription is honored by the pharmacist who fulfills the prescription. In another aspect, the invention provides methods and systems whereby customers, e.g., patients, can access a database containing information including prescription information, medical records, and the like for a variety of purposes. In another aspect the invention provides methods and systems for accurately tracking medication sample usage, thereby facilitating the ability of pharmaceutical sales representatives to provide appropriate numbers of samples to a multitude of sites in a timely fashion. In yet another aspect, the invention further provides methods and systems whereby subscribers, e.g., individuals working for pharmaceutical companies, can use the World Wide Web to access a database containing timely data regarding prescribing activity (e.g., number of prescriptions filled during a given time interval, number of prescriptions filled in a particular geographic region) for the medications they produce. In another aspect the invention provides methods and systems for targeted advertising.

DEFINITIONS

Figures 1, 2:
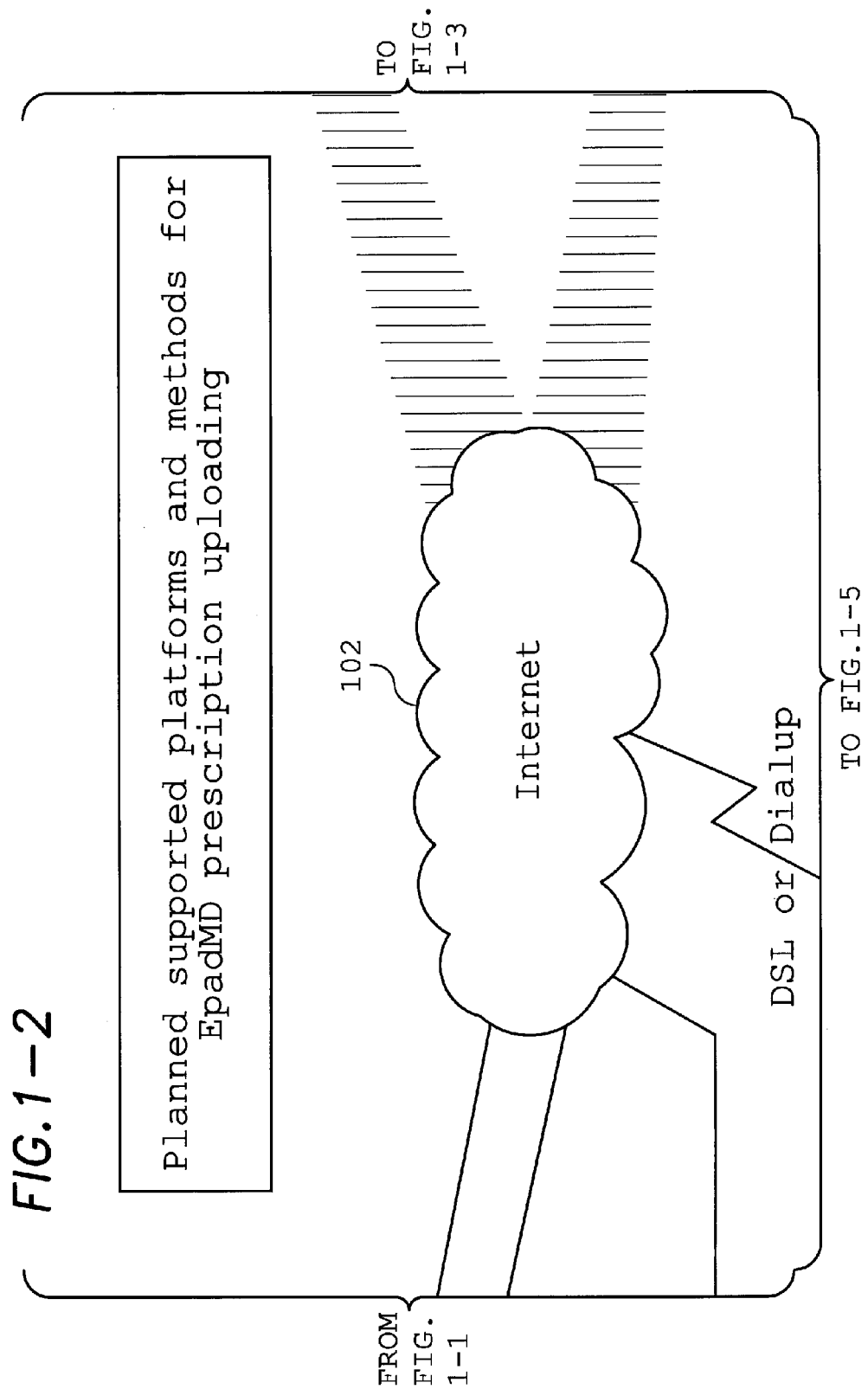
FIG. 1 is an overall schematic representation of the platforms and methods for prescription uploading in preferred embodiments of the invention.
FIG. 2 is a simplified schematic diagram of one embodiment of the present invention.

Bar code—As used herein, the term refers to any scannable, compact, representation of data, typically a series of lines of varying widths, spacings, and/or heights. The term includes 2D bar codes as described below and encompasses any currently available bar code formats as well as any that are invented in the future.

Created prescription—As used herein, the term refers to either a paper or electronic representation of sufficient information for a pharmacist to dispense a medication to a patient. Typically a created prescription contains prescription information such as, e.g., medication name, strength, dosage, quantity, prescriber name (signature), and prescriber registration number. Optionally the information can include number of refills and an indication of whether generic substitution is allowed as well as special instructions.

Corresponding to—As described herein, a bar code in a particular bar code format is decoded into a character sequence or reference number by a bar code scanner and bar code reader capable of interpreting bar codes of that format. As used herein, the bar code corresponds to that character sequence or reference number. In other contexts, a bar code corresponds to a database record for which that bar code's reference number serves as an identifier. For example, if a bar code reference number identifies a particular set of prescription information in a database, that bar code corresponds to the prescription record and corresponds to the prescription itself. The bar code also corresponds to the items of data stored in the record. For example, the bar code corresponds to the medication specified in the prescription.

Delivery—The process in which the pharmacist gives the medication to the customer (e.g., the patient). In the case of an Internet pharmacy, delivery includes sending the medication to the customer. Optionally, delivery can include a step of scanning a bar code on a label affixed to the medication container to be given to the patient and using the bar code to confirm that the correct medication container is being given to the customer.

Dispensing—The process in which the pharmacist transfers the appropriate amount of a medication from a supply container into a container to be given to the customer (patient). Optionally, dispensing can include a step of checking that the selected supply container bears a bar code corresponding to the medication specified in a prescription.

Enter—As used herein in reference to prescription initiating information or prescription information, to enter information includes any means of providing information including scanning a bar code, selecting among options (e.g., using arrow keys, clicking on buttons, etc.), clicking on a button (either a physical button or an icon of a button) to indicate acceptance of information, manually keying in information, etc.

Fulfillment—As used herein in the context of prescriptions, prescription fulfillment refers to the process by which a pharmacist provides medication to a consumer (patient) and includes the dispensing of medication from a supply container into a smaller container to be given to the consumer, recording the transaction, the act of giving the medication to the consumer (delivery), and any verification processes performed by the pharmacy. In the case of mail-order or on-line pharmacies it includes sending the medication to the consumer. When the consumer has received the medication, the prescription is fulfilled. In reference to prescriptions, the words fulfill and fill are used interchangeably herein.

Generating a bar code—As used herein, generating a bar code includes either or both of generating the actual bar code and generating a character string or reference number associated with the bar code.

Medication identification information—medication name, medication ID number, and/or a bar code assigned to the medication.

Patient identification information—patient name, patient ID number, and/or a bar code corresponding to the patient ID number.

Personal digital assistant (PDA)—As used herein the term personal digital assistant is taken to refer to any hand-held portable devices, including computing devices and cellular phones. Preferably the devices are capable of connecting to the Internet and exchanging information with remote server systems.

Prescriber—As used herein the term prescriber refers to an individual authorized to write prescriptions. In general, such an individual will have been issued a license and registration number within the geographic region (e.g., state) in which he or she practices. A variety of health care providers may be authorized, within certain contexts, to write prescriptions. In some cases this prescription writing authorization may be limited to certain settings or medications. At present most authorized prescribers are physicians, however the system is intended for use by any authorized prescription writer.

Prescriber identification information—prescriber name, prescriber ID number or registration number, and/or a bar code corresponding to either of these ID numbers.

Prescribing location or prescriber location—A location associated with a particular PDA or with which an individual is associated in his or her prescribing capacity, e.g., a physician's office, clinic, hospital or the like. Most commonly, a prescriber location is a place where a prescriber treats patients and issues the majority of prescriptions. It may also be a location at which pharmaceutical samples would be provided. A prescriber may have more than one prescribing location. It is not required that a prescriber have a location although generally most prescribers will have at least one location. The location may be a virtual location rather than a physical location.

Prescription fulfillment point—Any location at which a prescription may be fulfilled, including traditional outpatient pharmacies, hospital pharmacies, and Internet-based pharmacies. It is to be understood that references to pharmacies can encompass any of the aforementioned prescription fulfillment points.

Prescription information—As used herein, prescription information includes any or all of the following types of information:

(1) Patient identification (ID number and/or name)

(2) Medication identification (medication name)

(3) Medication strength—This information describes the amount of active ingredient per medication unit, e.g., 25 mg, 50 mg, 100 mg, 250 mg, etc.

(4) Medication format—This information designates the physical form of the medication, e.g., pill, tablet, capsule, liquid, etc.

(5) Medication dosage—This information includes amount of medication to be taken at each dosing time, dosing route, and dosing interval, e.g., 100 mg PO qd (100 mg by mouth once daily); 50 mg PO bid (50 mg by mouth twice daily); 1 tsp PO q.h.s. (1 tsp by mouth before going to sleep). Since these three items of information are related and are often thought of as a unit, it is logical to group them together.

(6) Medication quantity—Number of dosage units (e.g., tablets, bottles, etc.) to be dispensed (7) Refill number—number of refills authorized (8) Prescriber ID (e.g, name and registration number)

(9) Pharmacy ID (e.g., name and/or ID number)

(10) Generic substitution allowed—A (Y/N) item of information indicating whether the prescriber authorizes the pharmacist to substitute a generic version for a brand name medication.

(11) Special instructions

Prescription initiating information—As used herein refers to certain information required for the majority of prescriptions, and that is usually supplied at the beginning of the prescription creation process. In general, prescription initiating information includes patient identification information, prescriber identification information, and medication identification information. Note that prescription initiating information is, in most cases, a subset of prescription information.

Prescription status data—Prescription status data can include information indicating whether a prescription has refills remaining, whether the prescription is still valid (e.g., has not been canceled), and whether the prescription has been fulfilled. Some or all of the prescription status data can be included in the prescription information.

Sample dispensing location—Any location at which a sample may be provided to a patient, e.g., a physician's office or clinic. In most cases, a sample dispensing location will be a prescribing location.

Send—In reference to information or data, the terms "send" and "transmit" are used interchangeably herein, as are related terms such as "sending" and "transmitting" or "transmission". In general it is to be understood that sending and transmitting occur electronically, including either over a physical network or wirelessly.

Send a Web page—As used herein, sending a Web page includes sending an HTML (or other markup language) document. Sending a Web page also includes sending information entered onto a Web page (e.g., by clicking a submit button or the like). In the latter case, the entire contents of the Web page is not ordinarily sent but only certain data items along with additional information identifying the data items. This latter case is also referred to as submitting the Web page or submitting the information on the Web page.

Storing a bar code—As used herein, storing a bar code includes storing the information represented by a bar code, which could be a reference number, a character string, a large block of data (e.g., in the case of a 2D bar code). In addition, storing a bar code can include storing a representation of the lines that make up the bar code.

User—As used herein, a user may refer either to an authorized prescriber, an individual such as a pharmaceutical sales representative who has his/her own unit, or an individual such as a pharmacist or market researcher who has access to certain features of the inventive Web service or associated database(s) but who may not have his/her own unit. The user may also be an individual for whom a medication is prescribed and who can access the Web site of the present invention, e.g., from a personal computer or PDA equipped with a Web browser.

Web service—As used herein the term Web service refers to services performed by a Web server, Web server engine, Web site, or persons supporting or working in conjunction with such Web server, Web server engine, or Web site.

DETAILED DESCRIPTION OF CERTAIN PREFERRED EMBODIMENTS

The development of small, hand-held computers, or personal digital assistants (PDAs) has offered an alternative to the use of traditional or notebook personal computers. Such devices are commonly used for tasks such as maintaining a calendar, list of addresses, and other personal information. In addition, they may contain application programs such as word processing programs, enabling users to perform a wide variety of tasks in a completely mobile manner, without the inconvenience of transporting a notebook computer. It is a common feature of such devices that they can upload information entered therein to applications within a user's personal computer, in a process referred to as "synchronizing" or "syncing", thus enabling users to seamlessly integrate activities performed on mobile and traditional computer platforms. The synchronizing technology employed in the Palm line of devices is described in U.S. Pat. No. 6,000,000 to Hawkins, et al., entitled "Extendible Method and Apparatus for Synchronizing Multiple Files on Two Different Computer Systems", which is incorporated herein by reference. PDAs can be connected to personal computers in a number of different ways for the purpose of exchanging data. For example, the Cassiopeia suite of PDA products comes with a docking cradle via which information can be uploaded to a user's personal computer. Other PDAs such as the Palm line of devices upload data through a wireless infrared (IR) link. Other means of communication include local area network (LAN), wireless LAN, and bluetooth radio technology. Bluetooth radio technology, which operates in the unlicensed and therefore freely available ISM (industry, science, and medicine) band, is a newly emerging technology that offers the potential to replace many currently used proprietary cable systems with a universal short-range radio link. (See http://www.bluetooth.net for additional information.)

Access to communication media such as e-mail and the Internet is assuming a more and more important role in the daily activities of many members of the workforce. Efficient performance of many tasks requires access to e-mail and access to rapidly changing information available via the Internet. In addition, the vast store of information accessible through the World Wide Web and the increasing amount of business that is conducted via networked communications means that mobile Internet connectivity is becoming an essential tool in many professions. It is likely that physicians will routinely access informational Web sites (for example, MedScape at http://www.medscape.com) and databases, including databases containing patient records, results of lab tests, etc., via the Internet. The ability to access this information in a mobile manner will provide significant benefits in terms of enabling physicians to make informed, timely decisions regarding patient care.

Many PDAs offer such capabilities as e-mail sending and receiving and Internet connectivity through either a modem or a wireless interface. The number of Web sites offering content specially formatted for viewing on the small screen of the PDA is growing, and it is likely that it will be practical to view a significant subset of World Wide Web content via PDAs. In addition, many PDAs offer capabilities such as paging and fax receiving/transmitting services. Yet more recently cellular phones have started to offer many of the same capabilities as PDAs in terms of connecting wirelessly to the Internet and uploading information into personal computers, in addition to the traditional wireless phone services. Phones such as the Sprint PCS Data Phone offer messaging services, enabling users to receive and send e-mail messages. The NeoPoint 1000 Phone combines the functions of a wireless phone and a PDA within a single unit, and is probably an early example of a future trend towards integration of all communications media within a single portable, wireless unit.

The present invention encompasses the recognition that PDAs and wireless phones able to exchange data with a personal computer connected to the Internet and/or connect directly to the Internet represent, in many respects, an ideal platform on which to implement an electronic prescription creation system. Coordinating prescription creation through a World Wide Web server allows the storage and processing of large amounts of data (e.g., drug information, pharmacy addresses, etc.), thus overcoming the relatively limited storage and processing capabilities of PDAs. In addition, coordination via a Web server allows updates and changes (both to software and information) to be made only once rather than on a multitude of devices.

The invention provides a system that allows the entry of prescription information into a PDA by a prescriber, transmission of the prescription to a pharmacy, and notification by the pharmacy once the prescription is filled. In a preferred embodiment of the invention the prescriber provides information that identifies him or her as being an individual authorized to write prescriptions. The prescriber enters patient identification information and prescription information into the unit. After completing entry of the patient and prescription information into the unit, in a preferred embodiment of the invention the prescriber signs the prescription. Optionally the prescriber also enters pharmacy identification information into the unit, and this information is ultimately used to send the prescription information to the selected pharmacy. In a preferred embodiment the patient can also enter or change pharmacy identification information via the Internet. In a preferred embodiment of the invention a paper ticket containing prescription information is printed and given to the patient for presentation at the pharmacy. As described further below, the patient can present the ticket for fulfillment at any pharmacy, regardless of whether that pharmacy was previously specified.

To replace the written prescription, a mobile prescription entry system must adopt an approach that meets or exceeds the traditional system in terms of ease and speed of use from the point of view of the physician. The present invention encompasses the realization that by the utilization of bar code technology in conjunction with the mobile electronic devices described above, this objective can be achieved. Bar code technology provides a means of automating certain steps of prescription creation and of efficiently managing prescription-related information and other aspects of medication distribution. The use of bar codes to facilitate capture of prescription information and filling of prescriptions at a pharmacy has been proposed, as in U.S. Pat. No. 5,883,370 entitled "Automated method for filling drug prescriptions", which is herein incorporated by reference.

In a preferred embodiment the present invention provides a mobile, electronic prescription creation and transmission system in which patient and medication identification information is entered by scanning bar codes into a client system, in which bar codes are generated for each newly created prescription, and in which prescription information is stored by a server that coordinates transmission of the prescription to a pharmacy. FIG. 1 shows a diagram of the invention illustrating the platforms and methods supported in a preferred embodiment. FIG. 1 presents the invention from the point of view of prescription creation and transmission. Other aspects of the invention are presented in subsequent figures. Prescription information is entered into PDA 101 using a form-based approach, in which the prescriber enters data into designated areas (fields) of the PDA screen. In FIG. 1 elements 101a, 101b, 101c, 101d, and 101e represent alternative embodiments of a PDA, any or all of which may be used in the present invention. Although some of the information is entered by scanning a bar code, other sorts of information is entered through the use of menus, scrollable lists, check boxes, buttons, etc. Such elements are typical of graphical user interfaces, found in many application programs designed for use on PCs and are ubiquitous features of forms found on Web pages. In a preferred embodiment of the invention, after the prescriber indicates a medication, a form with fields displaying default prescription information is presented. The prescriber can accept the default values if appropriate. Alternatively, the prescriber can edit the fields as further described below. While the use of PDAs for prescription creation and transmission has been described, for example in U.S. Pat. No. 5,845,255 entitled "Prescription management system" and in WO9529455, entitled "Electronic Hand-held Prescription Writing and Transmitting Device", both of which are herein incorporated by reference, these systems did not contemplate the use of bar code technology for data management nor exploit the full capabilities of centralized management of prescription information. Nor did they offer the full coordination of prescription creation and fulfillment as achieved by the present invention.

As shown in FIG. 1, in preferred embodiments of the invention Internet 102 is used as the medium for transmission of the prescription information from the prescriber to the pharmacy and from the pharmacy to the physician. The information is sent from the prescriber's PDA over the Internet to a Web service 103 of the present invention, hereinafter referred to as the EpadMD Web service or the EpadMD Web site. In certain embodiments the prescription information is first sent from the prescriber's PDA to personal computer (PC) 104 connected to the Internet and is then sent to the EpadMD Web service. Communication between PDA 101 and PC 104 can take place over Ethernet 105 or other local area network (LAN). Such communication can also take place wirelessly. PC 104 is connected to Internet 102 via any of a number of means indicated by element 106, e.g., DSL, 56K modem, cable modem, etc. In other embodiments the prescription information is sent directly from PDA 101 to EpadMD Web service 103.

The EpadMD Web service stores the prescription information in a prescription database. In a preferred embodiment of the invention a database record is generated for each prescription. The database record contains fields that correspond to each item of prescription information in addition to other information such as billing and insurance information. In preferred embodiments of the invention the database record contains fields with headings such as "Drug Name", "Strength", "Dosage", "Quantity", "RefillNumber", and "GenericOK" among others. For example, in the case of a prescription for the medication Zestril (lisinopril), a drug frequently prescribed for hypertension, a physician might typically prescribe one 10 mg tablet to be taken by mouth twice a day. Using a paper-based prescription system, such a prescription would be written as: Zestril, 10 mg, 1 PO bid, #100, refills 3, substitution—No. The abbreviations are typical of those used by practitioners, e.g., PO (per os) standing for 'by mouth' and bid standing for 'twice daily'. This set of prescription information would be mapped into the database record as follows: Drug Name=Zestril, Strength=10 mg, Dosage=1 PO bid, Quantity=100, RefillNumber=3, special instructions=leave blank, GenericOK=No. Of course the representation of the prescription information as stored in the database may be different from the way the information would be presented to a human user. When a dataset containing prescription information is received at the Web service, the Web service creates a new record in the prescription database and enters the prescription information. In preferred embodiments of the invention the time and date of any changes, additions, etc. to the record for a prescription are stored so that they may be accurately tracked. In preferred embodiments of the invention Web service 103 sends a print job to printer 107 at the prescriber's location (e.g., via PC 104), causing the printing of a paper ticket including the prescription information and bar code in addition to other information that preferably includes physician name and DEA number, physician address, phone, and fax number, etc., which can be given to the patient.

When a particular pharmacy is designated for a prescription, the EpadMD Web service transmits certain information to the pharmacy. Referring again to FIG. 1, in a preferred embodiment of the invention Web service 103 transmits to pharmacy 107 all information required for a pharmacist to fulfill the prescription. However, in certain embodiments of the invention the Web service sends a reference number to the pharmacy, and the pharmacist accesses a Web page on the EpadMD Web server. The server engine uses the reference number as the key into a database containing the necessary information and transmits the information to the pharmacy. In addition to transmitting prescription information to the pharmacy, in certain embodiments the EpadMD Web service notifies a pharmacist, e.g., by paging.

As part of the process of filling a prescription, in preferred embodiments of the invention the pharmacist uses a client system to access the record for that prescription stored by the EpadMD Web service. Before the pharmacist gives the medication to the patient, in preferred embodiments of the invention various checking procedures are performed, as described below. When the pharmacist gives the medication to the customer, the pharmacist provides an indication to the EpadMD Web service that the prescription has been filled and picked up. The database is updated to reflect the fact that the prescription has been filled and picked up. Thus the present invention provides a database containing prescription information including prescriber name, prescribing information, and pharmacy, as well as a record of when each prescription is filled. In a preferred embodiment of the invention, the fact that the prescription has been filled is recorded in the database during the process of prescription fulfillment, thus ensuring that the database contains complete, up-to-date information regarding prescription fulfillment essentially at all times.

Electronically capturing and storing the prescription information offers a number of opportunities. In a preferred embodiment of the invention the prescription information is checked against the other prescriptions for that patient to identify situations in which drug interactions may occur. In certain preferred embodiments of the invention the prescription information is compared with information in the patient's medical record to determine whether any contraindications, e.g., prior allergic reactions, exist. In certain embodiments of the invention the prescriber is notified if an individual fails to fill a prescription. The prescriber can also be notified if a patient's prescription is close to running out, so that the prescriber can contact the patient if necessary. In other embodiments of the invention the patient may be notified before the prescription runs out and reminded to contact the prescriber so that the prescription can be renewed in a timely fashion.

As described in more detail below, in one aspect the present invention further provides a way for sales representatives to track the usage of samples by the prescribers to whom they distribute the samples. In another aspect the invention also provides for limited access to the prescription database by authorized individuals, e.g., individuals who are interested in obtaining marketing and sales data regarding prescriptions. In a preferred embodiment of the invention subscribers associated with a given pharmaceutical company can only view data pertaining to prescriptions for medications manufactured by that company. In another aspect the invention provides a system by which customers (e.g., patients) can view information pertaining to their prescriptions (and other medically related information such as medical records, insurance records, and the like). In preferred embodiments the customers can change or modify certain aspects of this information, e.g., they can select or change the pharmacy at which the prescription is to be filled.

Use of the World Wide Web and browser technology provides an access platform that can be utilized by all categories of users including prescribers, pharmacists, customers (e.g., patients), sales representatives, market researchers, and others. Access can be achieved using a wide range of hardware devices including both PDAs and personal computers. Users interact with the system using Web pages, a communication medium with a set of display and interaction conventions already familiar to many users. It is envisioned that prescribers will utilize their PDAs for a variety of purposes such as accessing sites that provide CME (continuing medical education) materials, organizing their calendar, keeping lists of phone numbers, etc. Some of these activities will operate independently of the invention while others are incorporated into certain preferred embodiments of the invention.

The detailed operation of preferred embodiments of the invention is described below. For ease of description, the working of the system is described primarily in terms of a prescriber in an outpatient setting prescribing a medication provided in the form of pills, tablets, etc. However, it is equally possible to use the system in other health care settings such as with hospitalized patients and with other forms of medications, e.g., liquids, creams, ointments, etc., to be administered by the patient or by a health care provider such as a nurse. The system provides for identification and authentication both for prescription creation and for other activities including those that may be carried out by nonprescribers (e.g., sales representatives, pharmacists) who will use the system; entry of patient identification information and medication identification information; entry of prescribing information and pharmacy identification information; transmission of prescription information from prescriber's PDA to EpadMD Web system and from the Web system to the pharmacy; reception of the prescription information by the pharmacy; utilization of bar code technology by the pharmacist to check to make sure the correct drug is being dispensed; transmission of information back to the Web site indicating that the prescription has been filled; and notification by the Web site to the prescriber or patient to provide information indicating that the prescription has or has not been filled, is about to run out, etc. The system provides methods for sample tracking, for obtaining up-to-date market-related data, and for permitting access by customers (patients) for certain purposes.

Since in preferred embodiments the EpadMD Web Service system utilizes bar code technology, the Internet and the World Wide Web, important features of these technologies will first be discussed. Then flow diagrams showing the flow of events in a particular embodiment will be presented, followed by descriptions of the EPadMD prescription server engine and prescription database and the processes of user access, identification and authentication for prescribers and nonprescribers, and information entry (i.e., patient ID, medication ID, and prescription information). Transmission of information between prescriber's PDA, the EPadMD Web server, and pharmacies is described. Data storage and processing at the EpadMD Web server is described, including the use of bar code reference numbers to identify and keep track of each generated prescription. Other features of the systems are also described. In order to focus on the most significant features of the invention, the flow diagrams omit certain steps such as generating error messages or handling exceptions.

Bar Code Technology

During the past 15 years the use of bar coding has expanded dramatically, particularly following the adoption of the Universal Product Code (UPC) as the standard for retail grocery stores. The increasing availability of personal computers and software capable of generating, processing, and printing bar codes has contributed to this growth. Bar codes represent a convenient, rapid, and easy means of entering and accessing data. (See "A Bar Code Primer: An Introduction to Bar Coding Symbologies, Reading and Applications", Worthington Data Solutions, Santa Cruz, Calif., 1998, which is herein incorporated by reference for additional information on bar codes and on software and hardware employed in bar code systems.)

Currently, typical bar codes are a series of vertical lines and spaces with varying widths and/or heights. Different combinations of bars and spaces represent different characters. In general, a bar code reader consists of a light-emitting scanner and a decoder. When a bar code scanner is passed over the bar code, the light emitted from the scanner is absorbed by the bars and reflected by the intervening light spaces. A detector (e.g., a photocell) in the scanner detects the reflected light and converts it into an electrical signal. The intensity of the signal varies depending on whether a line or a space is being scanned, and the duration of the signal corresponds to the width of the line or space. The bar code reader then decodes the digitized signal into the characters that the bar code represents and transmits the character sequence to the computer. In addition to scanning, decoding, and transmitting bar code data, most bar code readers notify the user of a "good read" by emitting an audible signal.

In most cases (i.e., most one-dimensional bar codes), the bar code itself does not contain any descriptive data but instead is just a reference number or character string that can be used by a computer to look up an associated database record that may be stored, for example, on the computer's hard disk or on a removable storage device such as a Zipdisk, floppy disk, etc. In the case of retail applications, the database record typically contains information such as price, item name, vendor name, inventory, etc. When a bar code is read by a bar code reader and transmitted to the computer, the computer can look up the price and also carry out actions such as adding the price to a subtotal, sending a command to a printer to print the name and price of the item, and updating the inventory. Thus the single act of scanning a bar code can trigger an array of activities.

A large number of formats for representing information using bar codes have been described. Among the most widely used formats are Code 39, Code 128, and UPC. Different formats differ in terms of the width and density of the lines and spaces used to encode characters, the set of characters that can be encoded, the length of the bar code, and various other parameters. Different formats are appropriate for particular applications, depending upon the type and quantity of information to be represented. In some cases industry standards dictate the choice of format. In general, the character string corresponding to a particular bar code will consist of numerical characters and will be referred to herein as a reference number.

Different types of bar code scanners vary with regard to the light source, the distance from which the bar code can be read, whether bar codes on curved surfaces can be read, etc. In preferred embodiments of the present invention a bar code scanner capable of scanning bar codes at a distance of preferably up to 18 inches, through laminated surfaces, and on curved surfaces is employed. To meet these requirements a laser scanner may preferably be employed.

The means by which a bar code reader interacts with data management software on devices such as computers or PDAs also varies. Typically bar code technology is integrated with data management systems through the use of a keyboard wedge interface or an RS-232 interface. Through the use of a wedge interface, the character sequence obtained by decoding a scanned bar code is provided to the computer in the same manner as if the character sequence had been typed on a keyboard. In the case of computers with external keyboards, a hardware wedge interface physically connects between the keyboard and the computer console and transmits characters from the decoder to the computer just as characters are transmitted from the keyboard. In the case of devices such as notebook computers that do not have an external keyboard, bar code character sequences can be transmitted to the computer via an RS-232 serial port such as the COM port on a PC. A software wedge takes in the scanned character sequence via the serial port and reroutes it to the keyboard buffer. Thus a variety of ways may be used to integrate the bar code scanner and reader with a computing device such as a PC. In certain embodiments of the invention the bar code scanner is built into the PDA (e.g., the Symbol 1700 & 2000 models). In other embodiments of the invention a PC card (PCMIA I or II) or a CompactFlash (CF) card can provide this functionality (e.g., cards manufactured by Socket Communications, http://www.socketcom.com).

Bar codes can be printed by modern dot matrix, ink-jet, and laser printers. A Wide variety of bar code fonts are available, allowing the printing of bar codes directly from word processors, databases, or virtually any other application program merely by switching fonts. For example, if a document is written using a popular word processing program such as Microsoft Word in which a bar code font has been installed, then typing a character string such as 13579 will result in insertion of the corresponding bar code into the document. Therefore creation and printing of documents containing bar codes requires merely that a font corresponding to the desired bar code format (e.g., Code 3 of 9, UPC) be installed on the computer. Bar code fonts can be obtained, e.g., from Elfring Fonts, Inc., P.O. Box 61, Wasco Ill. 60183. Extensive information about bar code fonts and different bar code formats can be found on the company's Web site (http://www.barcodingfonts.com).

Although conventional bar codes are one dimensional (1D) and are generally used to access data in a database, the desirability of encoding the data itself in bar code format has led to the recent development of two dimensional (2D) bar codes. Rather than merely encoding a relatively short character sequence, such bar codes can actually encode the data of interest itself. For example, the PDF417 2D bar code standard invented by Symbol Technologies (see, for example, "PDF417: The New Symbol of Data Management" at http://www.symbol.com/products, January, 2000, herein incorporated by reference), can carry up to 1.1 kilobytes of machine-readable data in a space no larger than a standard bar code. PDF417 bar codes can contain a wide variety of data formats including text, graphics, and biometrics. Systems for scanning and reading 2D bar codes are available. As a representative example, U.S. Pat. No. 5,988,508, entitled "Laser scanning system and scanning method for reading 1-D and 2-D barcode symbols" and herein incorporated by reference, describes a system for reading such bar codes. U.S. Pat. No. 6,005,945, entitled "System and method for dispensing postage based on telephonic or web milli-transactions" and herein incorporated by reference, describes a commercial use for PDF417 format bar codes. The present invention encompasses any and all bar code formats, including any that are invented in the future. Thus, in its broadest context, the invention encompasses any format for representing information in a compact, machine-readable manner.

Internet and World Wide Web

The Internet includes a large number of computers, computing devices such as PDAs, and computer networks that are connected through various communication links, over which they exchange information using such services as e-mail and the World Wide Web. The World Wide Web allows a server computer system (Web server or Web site) to transmit documents (i.e., Web pages) containing information to a remote client computer system, which can then display the Web pages. Both the server and client computers are provided with software to support World Wide Web interactions. Server systems run a web server application program, i.e., a web server engine. Client computers run a web browser, i.e., an application program that facilitates the requesting and displaying of World Wide Web pages. Internet-linked computers and Web pages are uniquely identified by a Uniform Resource Locator (URL) and/or IP (Internet Protocol) addresses. To display a Web page, a client computer issues a request including the URL for that Web page. The request is typically a HyperText Transfer Protocol (HTTP) request. HTTP is a protocol (i.e., a formal set of conventions governing the formatting and relative timing of message exchange between two communicating systems) that is used for World Wide Web communication. The request is sent over the Internet to the Web server that maintains the Web page. Upon receipt of the request, the server sends the requested Web page to the client computer for display by the client's browser.

Web pages are generally written in a programming language called Hypertext Markup Language (HTML), which consists in large part of a set of tags that define the manner in which the material contained between matching pairs of tags is to be formatted and displayed on the screen. HTML provides for the display of text, graphics, images, etc. In essence, when a client computer sends a request specifying a particular URL, the server sends back an HTML file containing the code that defines the Web page. This HTML code is interpreted by the client's browser and displayed on the screen. A key feature of HTML and of the World Wide Web is individual Web pages can be connected through elements known as links. When a user clicks on a link, which is typically represented by an image or highlighted word on the displayed Web page, the browser issues a request for a Web page specified in the link. The linked Web page is displayed on the client's screen. Thus links enable a user to conveniently "navigate" around the World Wide Web, moving from page to page within a Web site or from one Web site to another.

Originally HTML was generally limited to the display of static content on Web pages requested by the client. However, extensions to the language and the inclusion of programs (known as scripts) that can be run on either the client or the server side allow Web pages to behave in an interactive fashion, i.e., they provide the capability for response to user input. Form-based ordering systems (e.g., the on-line ordering system described in U.S. Pat. No. 5,960,411, "Method and System for Placing a Purchase Order Via a Communications Network", which is herein incorporated by reference) depend on this interactivity. In such systems, HTML elements such as check boxes, buttons, drop-down menus, etc., boxes, etc. allow users to indicate selections from a set of options presented on a Web page or enter text into designated fields. Web pages designed to accept user input typically contain a button (often referred to as a "submit" button) that the user clicks after entering data. Following submission, the data can be utilized by a script.

Scripts can execute a variety of actions in response to user input including, for example, the return of user-specified data retrieved from databases accessed by the server or the storage of user-provided information into server-side databases. Scripts can be written in a variety of languages (e.g., JavaScript, CGI/Perl). Microsoft's Active Server Pages is an application environment that facilitates the combining of HTML, scripts, and other components to allow creation of dynamic (non-static) Web pages.

As mentioned above, HTML is a markup language. HTML is actually a subset of SGML (standardized general markup language). Other subsets of SGML such as XML (extensible markup language) are coming into increasingly wide use for writing Web pages. Although in preferred embodiments of the invention Web pages are written using HTML, the invention also encompasses the use of Web pages authored in different markup languages.

Architecture and Flow Control of the EpadMD System

FIG. 2 is a simplified schematic diagram of one embodiment of the present invention illustrating the client/server nature of the system and providing additional detail regarding the server system. This embodiment supports the creation of prescriptions and other activities by prescribers, checking and updating of sample information by sales representatives, prescription-related activities such as entering desired pharmacy by customers (patients), market research activities by subscribers, etc. using client systems 201a, 201b, 201c, and 201d (PDAs, PCs, etc.) equipped with browsers 202a, 202b, 202c, and 202d. In general, any number and variety of client systems can be supported. The client systems communicate with EpadMD server system 205 over Internet 204. Access to information stored by the server system and the varieties of activity permitted to each user are determined based on ID 203a, 203b, 203c, and 203d in conjunction with a user password.

The server system 205 includes one or more server engines 206, a bar code generator 207, a prescription database 208 containing tables 209 for storing information, and Web pages 210 for interacting with users. Server engines 206, referred to hereafter as a server engine, can include World Wide Web servers, application servers (e.g., SQL servers), and proxy servers as shown in FIG. 1. The server system can also include additional databases such as patient record database 211 (which may contain lab results, medical history and progress notes for the patient, etc.) and drug information database 212 (which may contain information such as package insert, drug interactions, indications and contraindications for the medication, etc.). The Web pages include forms requesting identifying information such as name, registration number, etc., and forms providing prescription information options to prescribers.

Figures 1, 2, 3, 4:
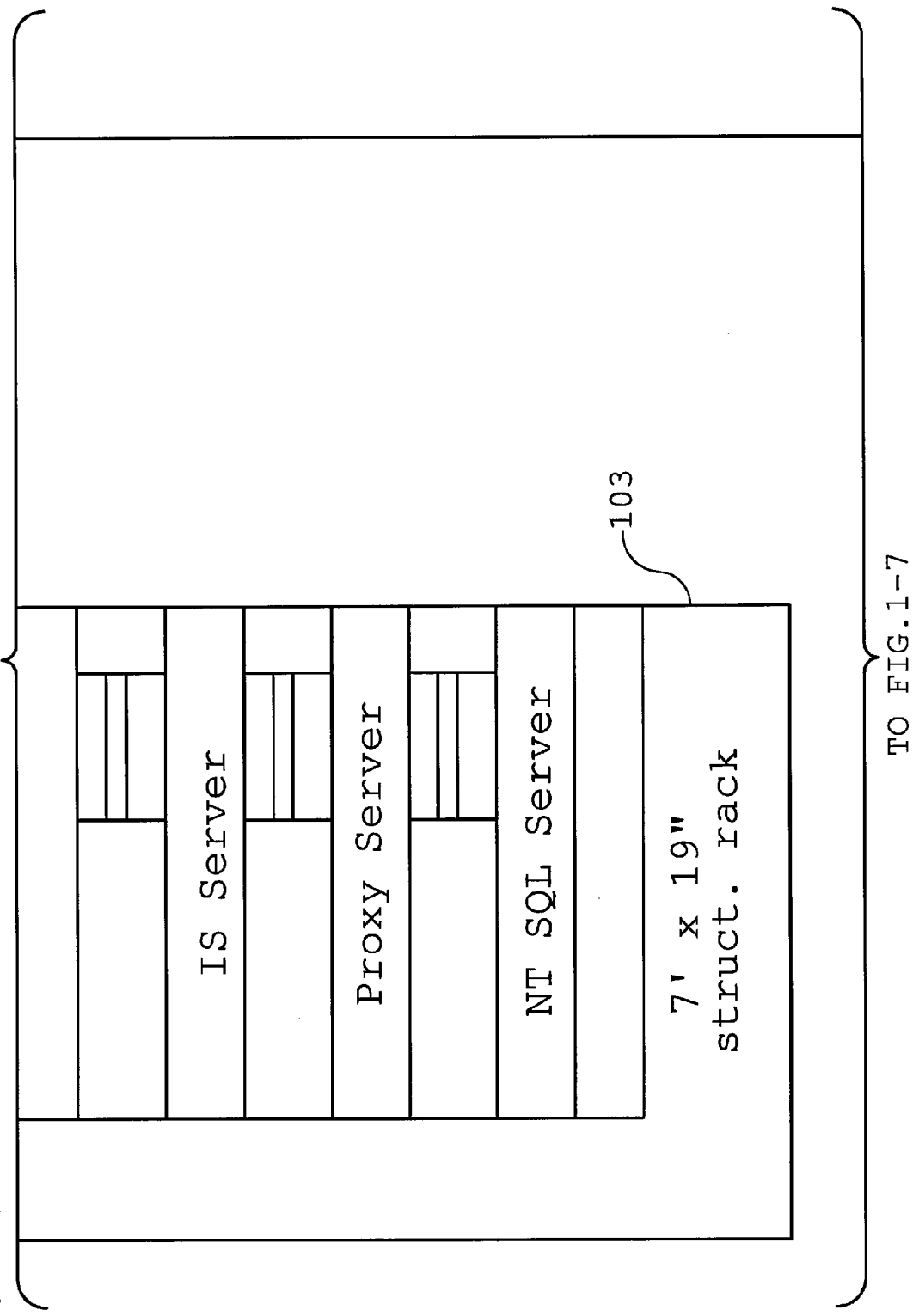
FIG. 3 is a flow diagram of the process for prescriber registration with the EpadMD system, from the point of view of the server system.
FIG. 4 is a flow diagram of the process for prescription creation from the point of view of the server system.

FIG. 3 is a flow diagram of a routine for prescriber registration (i.e., obtaining and checking identification information from a prescriber the first time the prescriber uses the EpadMD system) in a preferred embodiment of the invention, from the point of view of the server system. First, in step 301, the server receives a request from a client system (e.g., a PDA) to gain access to the EpadMD Web site. To gain access, the client system transmits an HTTP request including the URL of the Web server. In step 302, the server engine sends one or more Web pages back to the PDA requesting the user to enter identifying information, e.g., name and registration number and optionally additional information such as social security number. The user enters appropriate information and submits the Web page to the server engine, which receives the information in step 303. In step 304, the server engine compares the user-provided information. For example, the server engine compares the registration number with a list of valid registration numbers and determines whether a match is found. If a match is found, then in step 305 the server engine requests the prescriber to select a UserID and password. The server engine stores information including the UserID, password, name, and registration number in the prescriber table in step 306. In step 307, the server stores a client identifier ("cookie") in a file on the client. If a match is not found, then in step 308 the server engine sends an error message to the client and then issues another request for entry of the registration number.

FIG. 4 is a flow diagram of a routine that allows creation of a prescription, from the point of view of the server system. In step 401 the EpadMD server receives an access request from a browser on the client system (e.g., a PDA). In step 402 the server checks the identity of the client system, and in step 403 requests entry of a password. In step 404 the server receives and processes information indicating the activity selected by the user (e.g., prescription creation). In step 405 the server requests initial information needed for the prescription (prescription initiating information). In a preferred embodiment of the invention the server engine sends a form (e.g., a Web page) prompting the prescriber to enter patient ID and medication ID. In a preferred embodiment of the invention this information is entered by scanning bar codes. As described in more detail below, the bar codes may be scanned from a variety of sources including patient records, sample packages, or charts. In step 406 the server receives the requested information, and in step 407 the information (preferably a bar code reference number) is used to locate appropriate prescription information for that medication in the prescription information table. In step 408 the server engine assembles a form (e.g., a Web page) containing the prescription information options stored in the prescription information table and sends the form to the prescriber's PDA. The prescriber makes appropriate selections, which are received by the server in step 409. In step 410 a bar code for the prescription is generated, and in step 411 the selected prescription information and the bar code are stored in the prescription table. In step 412 the server engine sends a print job to a printer located at the prescriber's site. The print job includes the prescription information, including the bar code.

Figures 1, 2, 3, 4, 5, 6:
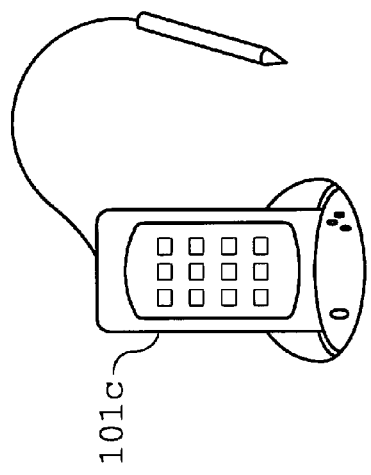
FIG. 5 is a flow diagram of the process for prescription transmission to pharmacy, filling of prescription at pharmacy, and transmission of notification to EpadMD server engine from the point of view of the pharmacist (client system).
FIG. 6 is an image representing a screen from which the prescriber can select various activities.

FIG. 5 is a flow diagram of certain steps in one prescription fulfillment scenario, from the point of view of the pharmacist and client system located at the pharmacy. Prior to step 501, the server engine has received and stored completed prescription information entered into a form or forms by a prescriber.

In step 501 the pharmacy client system receives the prescription information. Preferably the server sends information sufficient for filling of the prescription, but in certain embodiments the initial information received by the pharmacy client system is a bar code that can then be used to retrieve prescription information from the EpadMD web site). In any case, step 501 represents the receiving of sufficient information for fulfilling the prescription. Optionally the server system notifies a pharmacist at the preferred pharmacy (e.g., by paging) that a prescription is being transmitted to the pharmacy. In step 502, the pharmacist receives a paper ticket containing the prescription bar code from the customer (e.g., the patient). In step 503, the pharmacist accesses the EpadMD Web site and, in step 504, selects prescription fulfillment as the desired activity. The server engine sends a Web page to the pharmacy asking the pharmacist to scan the bar code on the ticket, which is done in step 505. In a preferred embodiment of the invention scanning the bar code triggers a prescription confirmation request to the server. The server engine uses the bar code reference number to retrieve the corresponding prescription information from the prescription table and determines whether the prescription should be confirmed, e.g., by checking the prescription status data. In alternate steps 506a or 506b, the pharmacy client system receives a Web page indicating confirmation or denial of the prescription. If the prescription is confirmed, the confirmatory Web page can include the prescription information itself, which the pharmacist can compare with the paper ticket and/or print out for the pharmacy's records or for the patient. Assuming the prescription is confirmed, then in step 507 the pharmacist prepares the medication according to the transmitted prescription information. In a preferred embodiment, before dispensing the medication, the pharmacist scans the bar code on the pharmacy stock supply container from which the medication is to be dispensed, and this bar code is sent to the Web server. The server engine checks the bar code from the stock container against the prescription information and alerts the pharmacist if the medication indicated by the container bar code does not match the medication indicated in the prescription information. In step 508 sends the server engine an indication that the prescription has been fulfilled, and in step 509 the pharmacist gives the medication to the patient, and in. The server system updates the prescription database, e.g., the prescription status data, to reflect the fact that the prescription has been filled. In the event that the server engine does not confirm the prescription, the server engine sends a Web page to the pharmacist reflecting this fact, and in step 510 further inquiry is performed. In the event that the pharmacist determines that the prescription information on the ticket does not match the prescription information provided by the EpadMD Web service, then further inquiry is likewise performed.

It is noted that variations within this sequence are within the scope of the invention. For example, if the prescription is transmitted to the pharmacy before the patient presents the ticket, the pharmacist may prepare the medication in advance of the customer's arrival. In this case, the pharmacist can perform the prescription bar code and the bar code on the stock supply container before the customer presents the ticket, i.e., at the time the medication is dispensed. The other part of prescription confirmation, i.e., the checking of the prescription status data performed by the EpadMD Web service, is performed later, when the customer presents the ticket. In preferred embodiments of the invention a label including a bar code providing medication identification (and additional information such as patient instructions for taking the medication) is affixed to the container to be given to the patient at approximately the time the medication is dispensed. This bar code can be scanned and compared with the bar code on the ticket to ensure that the correct container is given to the patient.

Further details of the steps outlined in the flow diagrams are provided below, following a description of the prescription server engine and the prescription database. It is to be understood that the flow diagrams represent only one possible embodiment of the invention and do not include all features of the invention, e.g., error handling. Additional steps and/or alternate orderings are within the scope of the invention.

Prescription Server

The prescription creation system of the present invention includes a prescription server that acts as a central site for the distribution and storage of prescription information, among other activities. As used herein, the term "server" is intended to include a single server, multiple servers, and accessory data storage devices accessible by such server(s). In a preferred embodiment of the invention the server is a World Wide Web server connected to the Internet and equipped with server software, referred to herein as a server engine. In a particularly preferred embodiment of the invention the server is a Web server running Microsoft's Internet Information Server (IIS) software under Microsoft's NT operating system. However, the server can employ any of a number of technologies commonly used in Web server development, for example Apache HTTP Server software running under the Unix, Linux, or other operating systems. The prescription server communicates over a data communication network with a plurality of remote computing devices, including PDAs and PCs, located at points of prescribing activity and points of prescription fulfillment.

The server engine accesses data of several different kinds. These data are stored in one or more databases which may be implemented in a variety of ways. In a preferred embodiment of the invention the data accessed by the server is stored in a relational database referred to as the prescription server database, containing multiple data tables. In a preferred embodiment the database uses Structured Query Language (SQL). SQL allows users to define, access, and manipulate data in a wide range of relational database management systems, such as Oracle, Sybase, Informix, Microsoft Access, and others. It should be understood that the data may be stored in separate databases, including databases accessible over a data communications network, and that other types of databases (e.g., object-oriented databases) could be used in the invention. However, for purposes of description it will be assumed that the data are stored in a relational database in multiple tables. The prescription server database is described further below.

Prescription Server Database

In a preferred embodiment prescription server database 208 (see FIG. 2) is an SQL database consisting of a set of tables, each of which consists of multiple records containing fields in which data is stored. One field in each record (or a combination of fields) constitutes a "key", i.e., an item (or items) of data that uniquely identifies that record. In a preferred embodiment the tables include, but are not limited to: a medication table, a prescription table, a prescriber table, a prescriber location table, a patient table, and a pharmacy table. Preferred embodiments of these tables are described below. It is to be understood that the descriptions below are for exemplary purposes only. Tables 209 of the invention may contain additional fields or a subset of the fields described below. Additional tables may be implemented (e.g., to support access by individuals performing market research), and different keys may be employed. In preferred embodiments of the invention the tables will contain standard fields such as creation time stamp, update time stamp, archive time stamp, and various status flags.

(i) Medication Product Table

Records in the medication product table contain names of medications approved (e.g., by the U.S. Food and Drug Administration or other regulatory agency) for administration to patients as well as bar code reference numbers corresponding to these medications. Preferably the table includes at least 80% of such medications, more preferably at least 90%, yet more preferably greater than 95%, and most preferably essentially all approved medications. Many medications may be formulated into a variety of different final products. For example, a medication may be manufactured in various strengths (e.g., number of milligrams) and formats (e.g. capsules, tablets), with each strength and format being a different product. As described above, each medication product is assigned a unique bar code by the manufacturer thereof (known as an NDC bar code). Thus a single medication may be assigned more than one bar code if it is formulated into more than one final product (e.g., 10 mg tablets of Zestril will have a unique bar code, and 20 mg tablets of Zestril will have a unique bar code). However, a given bar code is never assigned to more than one medication. Thus, a bar code reference number can be used to uniquely identify a particular medication product and the medication contained therein. The bar code reference number serves as the key to the medication product table. Therefore, each record contains a unique bar code, but multiple records may contain the same medication name. Fields in the medication table include, but are not limited to: bar code reference number (NDC bar code), medication name, strength, format, and manufacturer. The table may include both chemical name and trade name, information about whether a medication is a generic or brand name medication, and information about whether generic equivalents exist. It is noted that although the NDC bar code assigned by the manufacturer can be conveniently used in the practice of the invention, the invention is not limited to using NDC bar codes or using manufacturer-assigned bar codes. In certain embodiments of the invention the EpadMD system can assign bar codes. In addition, the invention can accommodate such bar code assignments as may be made to medications in the future.

The prescription server database also includes a table containing appropriate sets of prescription information for each medication product. As described in the Definitions section, the term "prescription information" includes medication strength, dosage, quantity, special instructions, etc. Not all items of possible prescription information need to be included for every medication. For example, not all medications will require special instructions. In general, prescription information will include those items which would be required for a prescriber to write a complete prescription for the medication. Of course for most medications different prescription information will be appropriate in different situations. The strength, dosage, etc. will generally vary depending upon the specific condition for which the medication is being described, the severity of the condition, the weight of the patient, etc. However, for many medications there is a standard dose, and for most medications there is a limited range of doses that is generally prescribed. One skilled in the art, i.e. a physician, is able to identify commonly used prescribing regimens for each medication. These commonly used prescribing regimens are stored in the prescription information table. As described herein, each medication product is assigned a bar code by the manufacturer. For each medication product, the bar code reference number serves as the key to identify the record containing prescription information for that medication product.

(ii) Prescriber Table

The prescription server database includes a prescriber table containing a record for each authorized prescriber. Fields in the record include: prescriber name, prescriber registration number, and prescriber PIN. The prescriber registration number (or a different unique number assigned to each prescriber) and prescriber location number (see prescriber location table) combination can be used as the key. If bar codes are assigned to prescribers then rather than using the registration number, a unique number corresponding to the bar code would be assigned to each prescriber. The table may also include additional information such as prescriber location number (see below), telephone number, etc.

(iii) Prescriber Location Table

The prescriber location table includes a record for each location at which users of the system may prescribe. A prescriber location number is assigned to each location and is used as the key. The fields of each record in the prescriber location table include: location number, street, city, state, zip code, phone number, fax number, and e-mail address.

(iv) Patient Table

The patient table includes a record for each patient that has been entered into the EpadMD system. A patient can be entered the first time a prescription is written for the patient or at any convenient time. Patient entry is preferably via a form-based approach. In a preferred embodiment of the invention the prescriber or an assistant enters patient information into Web pages transmitted from the EpadMD server engine. A bar code and reference number are assigned to each patient. The bar code reference number (patient ID) is used as the key. The fields of each record in the patient table include: patient ID number, social security number, name, billing street address, billing city, billing state, billing zip code, home street address, home city, home state, home zip code, home phone number, work phone number, e-mail address, driver's license number, insurance company, group number, plan number, insurance phone number, insurance fax number, and insurance e-mail address.

Additional information such as patient allergies, contraindications to certain medications, etc., may also be included in the patient table. In preferred embodiments of the invention such information, in addition to other patient information such as lab results, physician notes, etc., is accessible in the form of a virtual patient medical record.

(v) Pharmacy Table

The pharmacy table includes a record for each pharmacy that belongs to the EpadMD system. A pharmacy number is assigned to each pharmacy and is used as the key. The fields of each record in the pharmacy table include: pharmacy number, pharmacy name, street, city, state, zip code, phone number, fax number, e-mail address, opening time, and closing time.

(vi) Sample Inventory Table

The sample inventory table includes a record for each location at which samples may be dispensed. The fields of each record in the sample inventory table include: location number (see prescriber location table, medication name, and quantity. The location number and medication name serve as the key to the table.

(vii) Prescription Table

The prescription table includes a record for each prescription that has been created using the EpadMD system. In a preferred embodiment of the invention the fields of each record in the prescription table include: bar code reference number, medication name, strength, dosage, format, quantity, genericOK, patient ID number, prescriber ID number, pharmacy number, refill number, fill number, valid (yes/no). The bar code reference number, which is generated for each prescription, is used as the key to the table. The 'fill number' field maintains a count of the number of times the prescription has been filled by a pharmacist and is used to ensure that a prescription is not refilled beyond the number of times allowed by the prescriber. In addition, by keeping track of the number of times the prescription has been filled it is possible to minimize the potential for fraud (e.g., photocopying prescription tickets). The 'valid' field is used to invalidate prescriptions in the event that a PDA is lost or there is reason to believe that it has been used by an unauthorized individual to create prescriptions. The last three items, i.e, the refill number, fill number, and valid fields, constitute prescription status data.

User Access to the EpadMD Web Service

In certain embodiments of the invention each PDA will have, among its application programs, an application program of the present invention, referred to herein as "Epad" and a Web browser. When the Epad application is selected it automatically launches the Web browser, which contacts the EpadMD Web service. In certain embodiments of the invention a user accesses the EpadMD Web service by entering the URL of the EpadMD Web site into the browser. The site can be bookmarked, allowing for convenient access. In some embodiments of the invention the prescriber accesses the EpadMD Web site by selecting one of the built-in buttons provided on the PDA.

Figures 1, 2, 3, 4, 5, 6, 7:
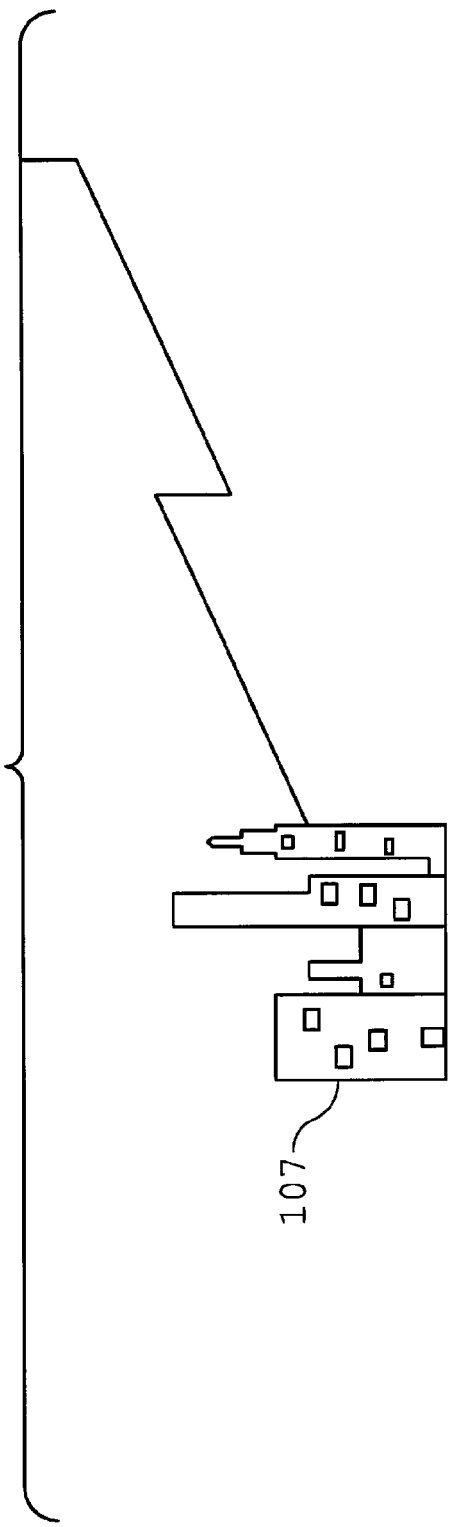
FIG. 7 is a screen shot showing a screen from which the prescriber can select various activities in a preferred embodiment of the invention.

Upon accessing the EpadMD system, the user is presented with a variety of options. The first time a user enters the system, the user is asked to supply identifying information. During subsequent interactions, the user is presented with a variety of options depending upon his or her status (e.g., whether he or she is a prescriber, sales representative, pharmacist, patient, etc.) For example, if the user is a prescriber, he or she may be offered options such as "create prescription", "dispense sample", "view prescriptions", "view patients", "view medications", "insurance information", "virtual medical records", "dictation", "CME", etc. As shown in FIG. 6, in a preferred embodiment of the invention options 602 are presented as text and/or icons on Web page 601. By clicking on the appropriate area of the PDA screen the user can select the desired option. In a preferred embodiment of the invention the options are links to Web pages from which the desired option can be performed. It is to be understood that a wide variety of user interfaces are within the scope of the invention, and the figure is for exemplary purposes only. The options may be presented to the user hierarchically, for example, the user may select a "View" button and then be presented with a set of options as to what sort of information is to be viewed. Additional links 603, e.g., to Web sites containing medical information, may be provided. FIG. 7 is a screen shot showing a screen from which the prescriber can select various activities in a preferred embodiment of the invention.

Although for prescribing purposes the EpadMD Web service is usually accessed via a PDA, the service can also be accessed from PCs or any other devices capable of connecting to the Internet.

Prescriber Identification and Authentication

In the current paper-based system, prescribers must transcribe their license number onto a prescription in order for the prescription to be authorized. The license number in combination with the prescriber's signature serves as confirmation that the individual writing the prescription is an authorized prescriber. It is essential that a computer-based prescription creation system offers a means of assuring that only authorized individuals are able to write and transmit prescriptions. The first time an individual accesses the EpadMD Web site the Web service requests certain information from him, which serves in the future to identify the individual and to determine the manner in which the individual may utilize the system. For example, the Web service asks the user to indicate whether he or she is a prescriber, a pharmacist, a sales representative, etc. Each prescriber is asked to provide his or her name and registration number. The server checks to confirm that the name and registration number correspond to an individual who is authorized to prescribe medication. If so, the Web site prompts the prescriber to select a userID and a personal identification number (PIN), preferably one that would be difficult for others to guess, that will serve to uniquely identify the prescriber during future sessions. The server may also may request additional information such as office address and phone number, e-mail address, etc. These items are stored in tables within the EpadMD database. In a preferred embodiment of the invention the server requests information from the prescriber by transmitting a Web page containing fields for the prescriber to enter the required information as well as a "Submit" button. When the user clicks on the "Submit" button, the data is transmitted to the server system. This type of interaction is used throughout the preferred embodiment of the invention, for the transmission and gathering of prescription information.

In a preferred embodiment of the invention the EpadMD Web server installs a so-called "cookie" onto the user's PDA. Cookies are a general mechanism that allows Web servers to both store and retrieve information on a client, e.g. a PDA or PC. When returning an HTTP object (e.g., a Web page) to a client, a server may also send a piece of information (cookie) which the client will store. Included in the cookie is a description of the range of URLs for which the cookie is valid. Any future HTTP requests made by the client which fall in that range will include a transmittal of the current value of the cookie from the client back to the server. In the case of the EpadMD system, the cookie contains information that is used by the EpadMD Web service in order to identify the prescriber and the PDA. The cookie may contain a prescriber's userID, registration number, the serial number of the PDA, and other information.

In a preferred embodiment of the invention a prescriber is prompted to physically sign and submit a form presented on the screen of the PDA. The prescriber's signature is stored in digital format by the EpadMD server engine for later use in verifying signatures on prescriptions created by that individual. Techniques for capturing and verifying digital signatures are known in the art and described, for example, in U.S. Pat. No. 5,818,955 entitled "Document and signature verification system and method" and U.S. Pat. No. 5,892,824 entitled "Signature capture/verification systems and methods", both of which are herein incorporated by reference. Such features are included in certain PDAs currently on the market such as the Palm VII.

When a prescriber accesses the system in the future, e.g. to create a prescription, the server requests entry of a PIN. The PIN is used to search a table containing the PINs, userIDs, and registration numbers of authorized prescribers. In certain embodiments of the invention, if a match between the entered PIN and a PIN in the table is found, the user is permitted to create prescriptions and is granted access to data specific for that prescriber, e.g., patient data for his or her patients. In certain embodiments of the invention, for increased security, the userID and registration number associated with the PIN are checked against the information stored in the cookie on the PDA that is being used by the prescriber. If userID and registration number match, then the user is permitted to commence prescription creation activity. If the userID and/or registration number corresponding to the PIN do not match the information stored in the cookie, the user must re-enter this information. Of course a variety of other means may be employed to identify and authenticate the provider. Other means of identification and authentication include the use of "smart cards" or biometric samples, both of which are well known in the art. Methods for making smart cards are described in U.S. Pat. No. 5,955,021 and references therein. A typical method for using smart cards is described in U.S. Pat. No. 5,983,273, and biometric sample (also known as biometric token)s are described in U.S. Pat. No. 5,870,723. The foregoing patents are incorporated herein by reference.

Identification and Authorization for Nonprescribing Purposes

In preferred embodiments of the invention a variety of individuals in addition to prescribers are able to access certain types of information available through the EpadMD Web site. For example, authorized individuals employed at a particular pharmacy are able to access prescription information pertaining to prescriptions to be filled at that pharmacy. Individuals employed at a particular pharmaceutical company that subscribes to the EpadMD Prescription Database Service are able to access prescription information pertaining to prescriptions for medications produced by that company. Sales representatives are able to access information pertaining to, e.g., lot numbers of medications that they have distributed as samples to physicians. Patients can use the system, e.g., to check prescription status, make or change pharmacy selection, get records for medical history or insurance purposes, or obtain reprints for lost or damaged prescriptions. Note that because the Web service is notified when a prescription is filled, the ability to obtain reprints of prescriptions cannot lead to inappropriate extra prescription filling. Thus, in a preferred embodiment of the invention at least five categories of individuals will have access to different types of information available through the Web site and will have different requirements in terms of the type of data that they will enter into the system.

Nonprescribers follow a similar process to that described above for prescribers in order to gain access to the EpadMD Web service. However, their access is limited to viewing and modifying only certain categories of information, and, of course, they are not granted the ability to create prescriptions.

In certain embodiments of the invention nonprescribers (for example sales representatives) will each have their own unit and will be able to enter a PIN directly into the unit in a similar fashion as described above for prescribers. In a preferred embodiment of the invention other users (for example individuals in the marketing department at a pharmaceutical company) will access the system by connecting to the EpadMD Web site via the Internet, e.g., through a traditional desktop or notebook computer. In certain embodiments of the invention prescribers and sales representatives will also interact with the EpadMD Web site, either to enter information or to review information that they are authorized to access, by means other than the mobile unit. For example, in certain embodiments of the invention databases of patient records are maintained on the Web site server or on other computers accessible via the Web site. It may be more convenient for a physician to review such records using a traditional computer with a large screen than with a mobile unit.

Information Entry by Prescriber

The creation of a prescription requires that the prescriber enter certain information including patient name (patient ID), medication name (medication ID), prescription information, etc. In general, patient ID and medication ID will be entered first. Patient identification entry is described first.

Patient Identification Information Entry

In a preferred embodiment of the invention each patient is assigned a unique bar code, preferably by the Web service of the present invention. Alternatively, such assignment can be performed by the institution where the patient receives health care as is already the case in many such institutions. Bar codes are widely used to identify medical records associated with the patient, including physician's history and physical examination notes, progress notes, lab test reports, reports of diagnostic studies, images such as X-rays, etc. Labels bearing the patient's name and bar code can be affixed to these records. In addition, the bar code can be displayed on a computer screen that is used to view patient records, etc.

In a preferred embodiment of the invention, after the prescriber has gained access to the prescription creation features, the system prompts the prescriber to enter a patient ID. In a preferred embodiment of the invention the prompt is provided by a Web page transmitted from the EpadMD Web server. Preferably the prescriber enters the patient ID by scanning the bar code assigned to the patient for whom a prescription is to be written. The bar code can be scanned from any patient chart or record that has been labeled with the bar code or, e.g., from a patient ID or insurance card on which a label bearing the bar code has been affixed. In the event that the scanned bar code does not correspond to a patient known to the system, an error message will be issued, and the prescriber will be prompted again to enter the patient identification information. In the event that there is no readily available source from which to scan the bar code, the prescriber uses the manual entry mode to enter the patient's name.

Medication Identification Entry

Following entry of patient identification information the prescriber enters information identifying the medication to be prescribed. In a preferred embodiment of the invention the prescriber enters this information by scanning a bar code into his or her PDA for entry into a Web page. In this regard it is noted that virtually every manufactured medication product is assigned a unique National Drug Code (NDC) bar code corresponding to both the name of the medication and to the particular dosage unit (strength and type of formulation, e.g. tablet or capsule). For example, there is a unique bar code for the 10 mg tablet formulation of Zestril and also a unique bar code for the 2.5 mg, 5 mg, 20 mg, and 40 mg tablets. This bar code is present on the exterior of medication containers supplied by pharmaceutical manufacturers, e.g., containers containing large numbers of pills, tablets, etc. sold as supply stock to pharmacies. A bar code is also present on the exterior of sample packages, from which the identity of the medication can be determined.

The medication bar code can be scanned from a variety of sources. For example, the patient's medical record may contain paper copies of prescriptions previously created using the present invention, and these will bear the medication bar code. In certain embodiments of the invention the prescriber scans the bar code from a chart or booklet containing names of medications and corresponding bar codes. The inventive system provides such charts and booklets. Charts may be provided in a vertical format, convenient for hanging on a wall or the back of a door. They may be laminated for durability. They may also be provided in a foldable format or as booklets. In a preferred embodiment of the invention updated versions of such charts or booklets are made available in the event that a new medication product becomes available. As an interim measure, stickers bearing the name and bar code of newly available products can be provided pending the production of updated charts. One skilled in the art will readily be able to determine the size and spacing requirements of the bar codes necessary in order for such a chart to be accurately scanned. In another embodiment the medication information is scanned from a sample package.

In another embodiment of the invention a Web page (or, in certain embodiments, a custom GUI program on the PDA) provides a drop-down list of medications from which the prescriber can make a selection. Additionally, a free-form field can be provided for medications that are not in the list, for which no bar codes are available, or medications that are not yet in the server or PDA database(s).

Prescription Information Entry

Figures 1, 2, 3, 4, 5, 6, 7, 8:
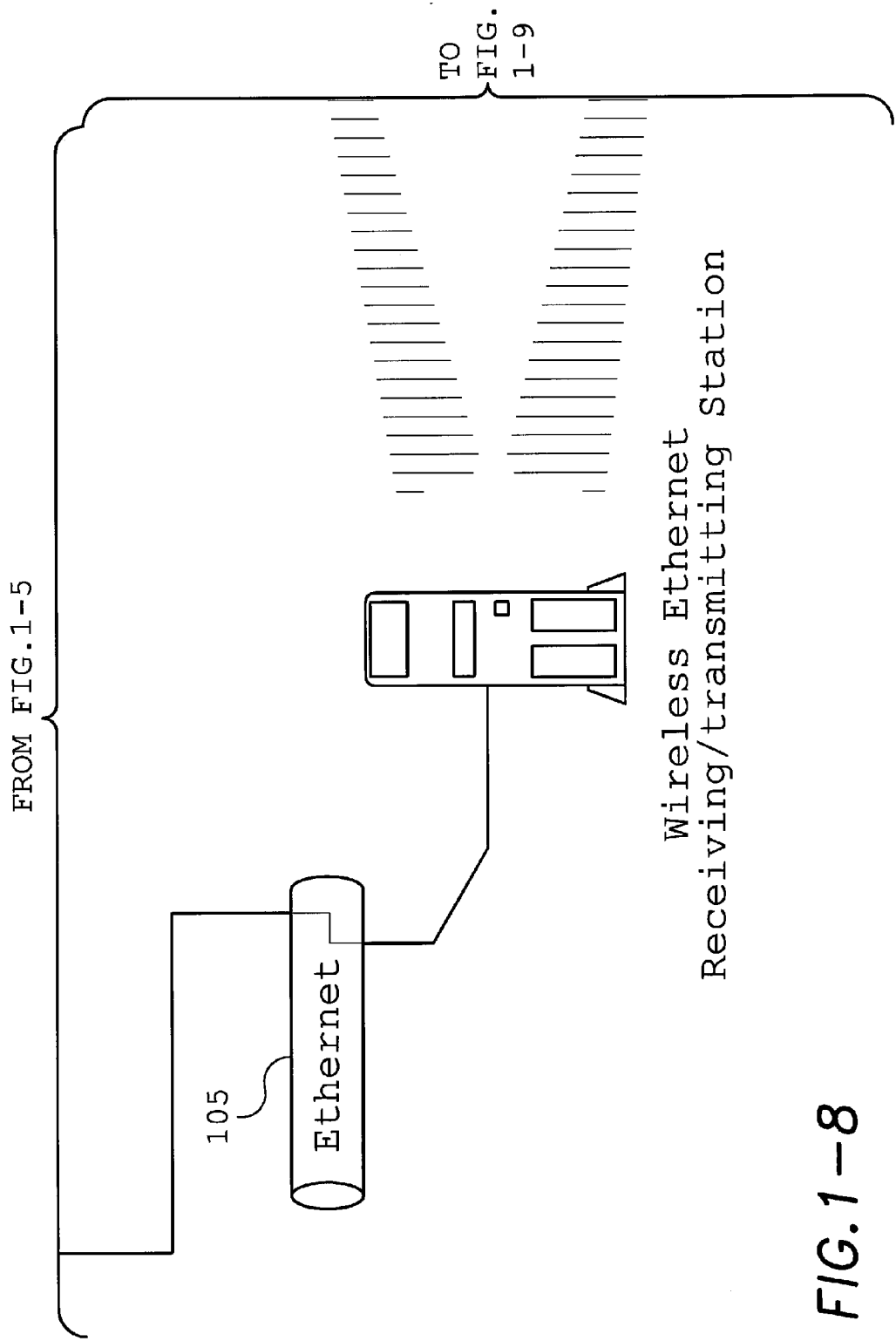
FIG. 8 is an image representing a form displaying prescription information for a prescription for Zestril, 10 mg, bid.
Figures 1, 4:
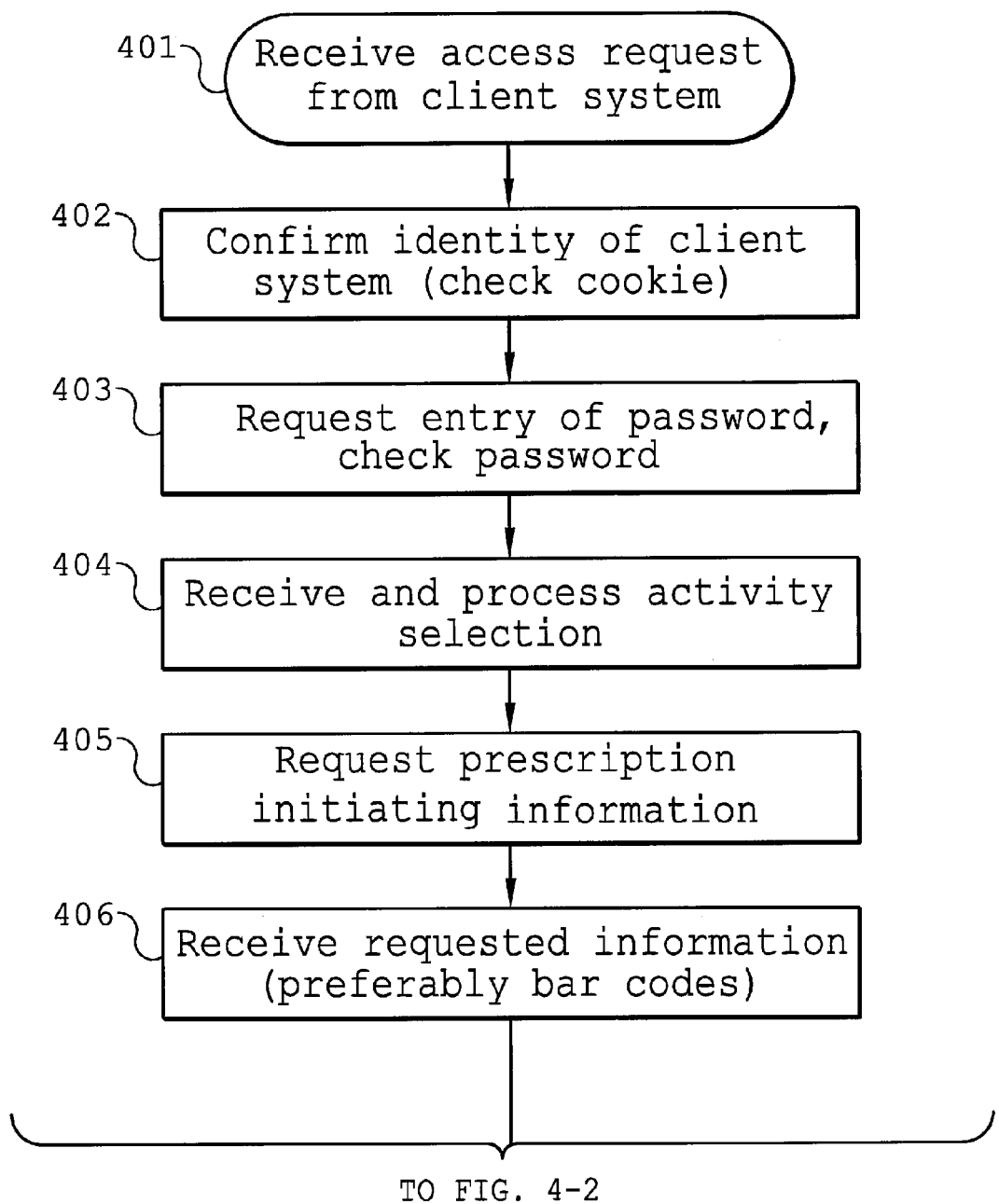
Figures 1, 5:
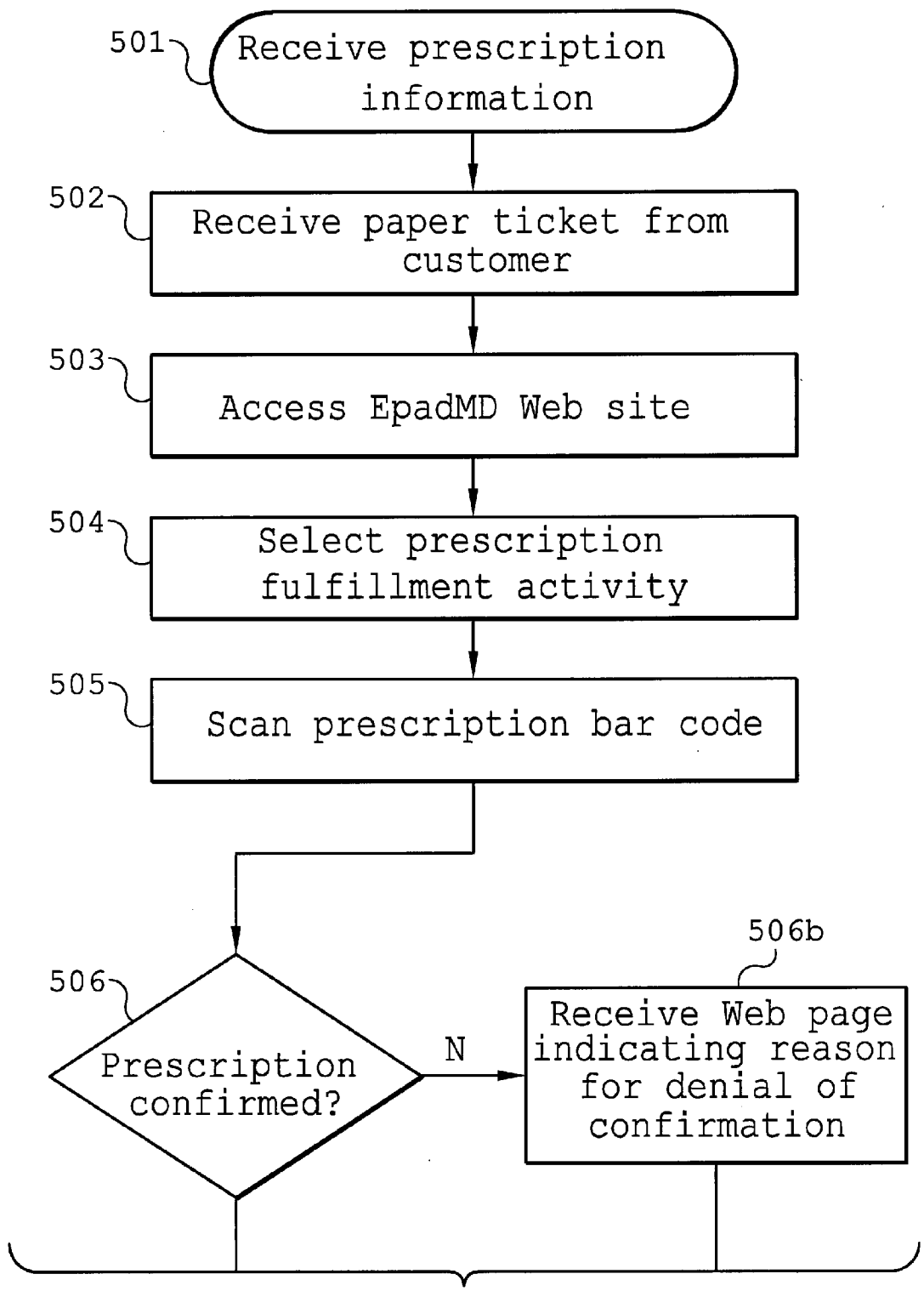
Figures 2, 5:
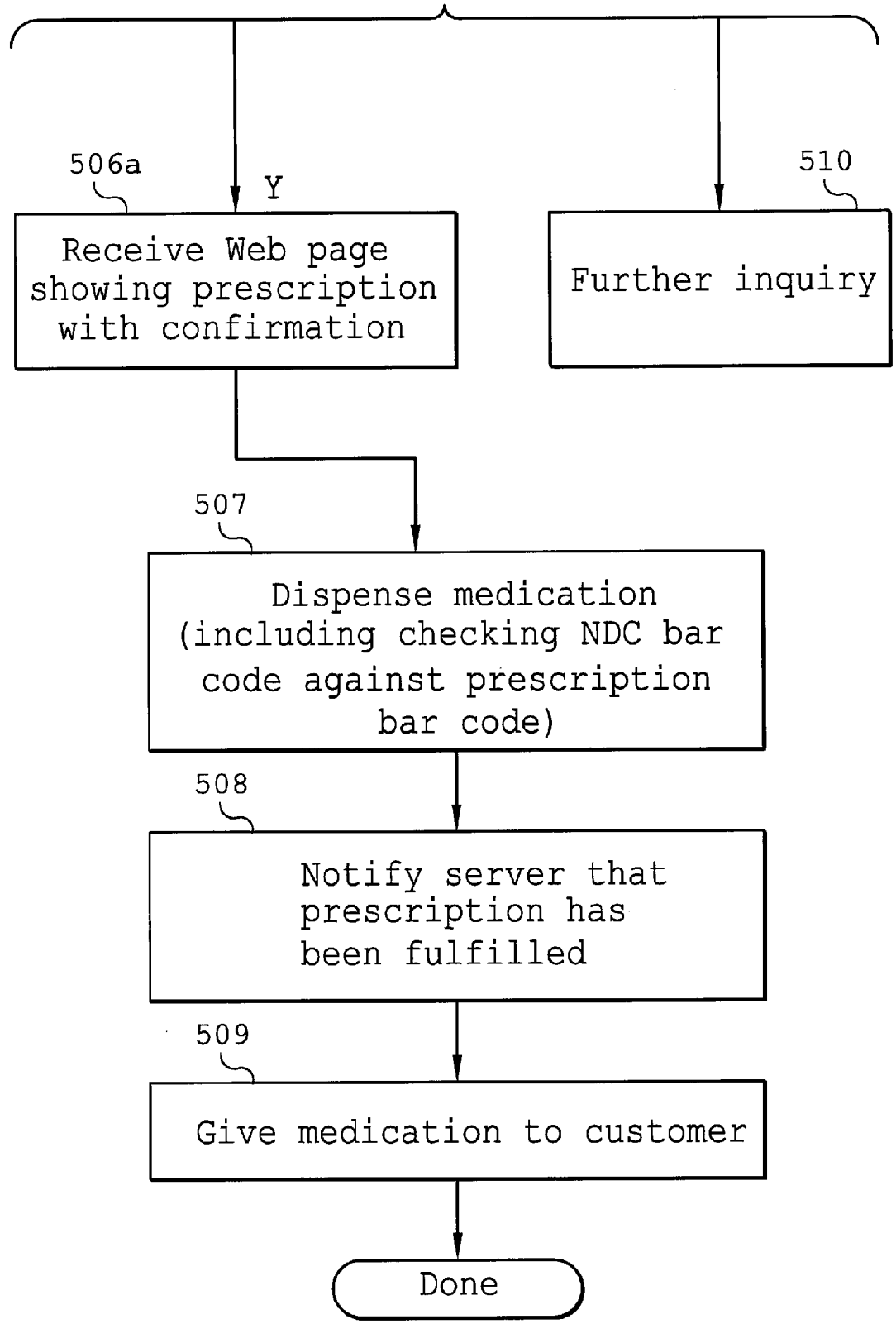
Figure 6:
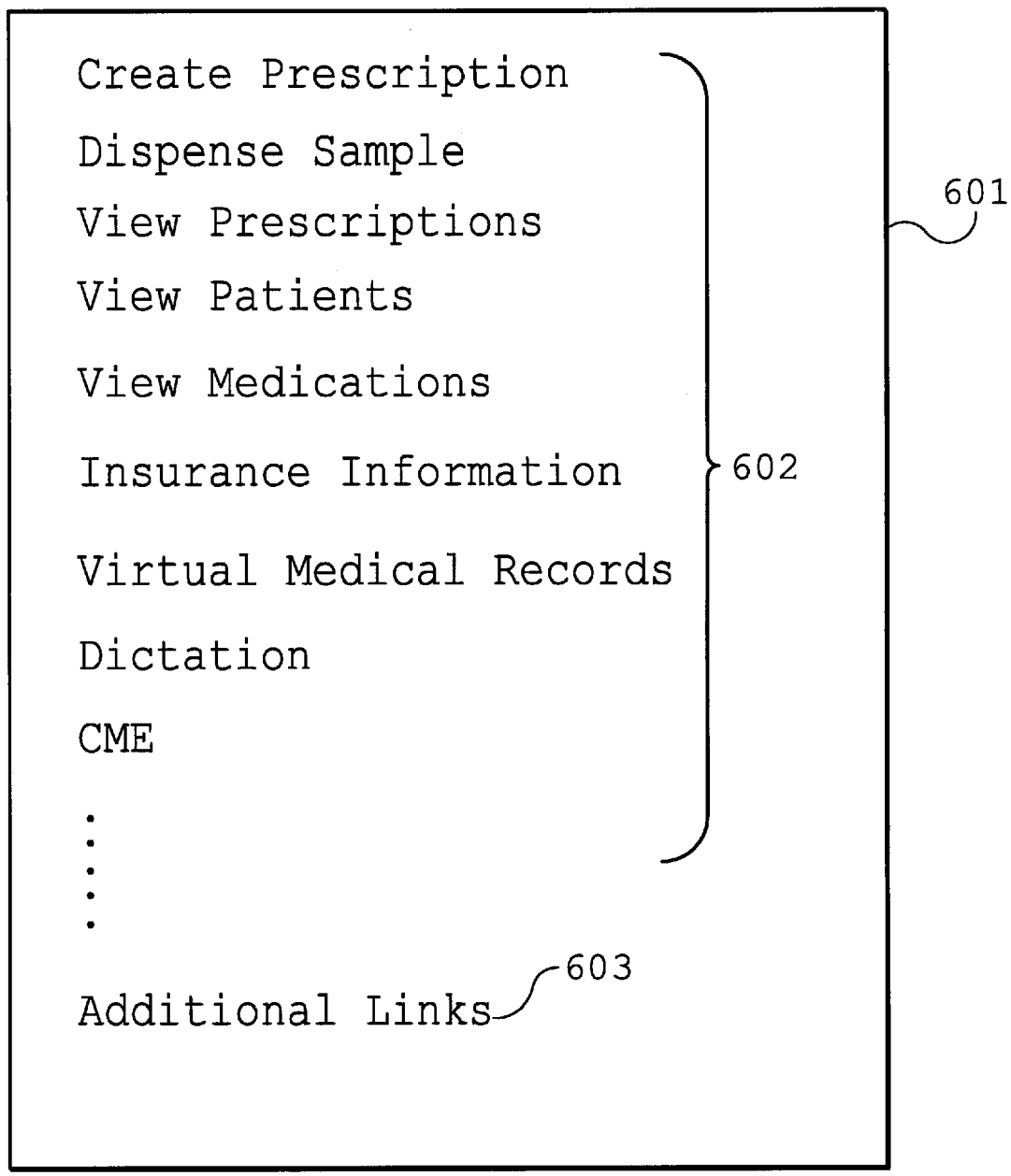
Figure 7:
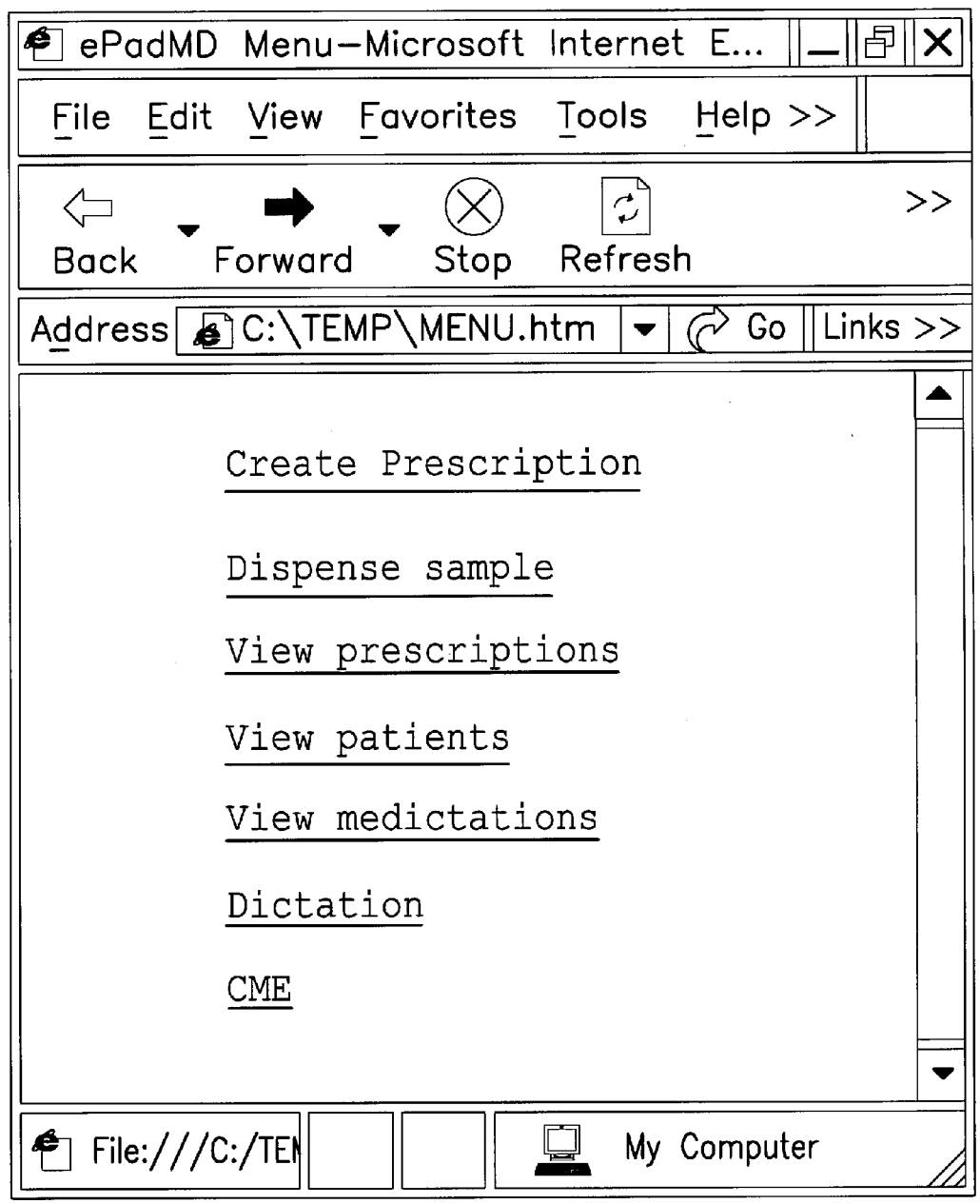
Figures 1, 9:
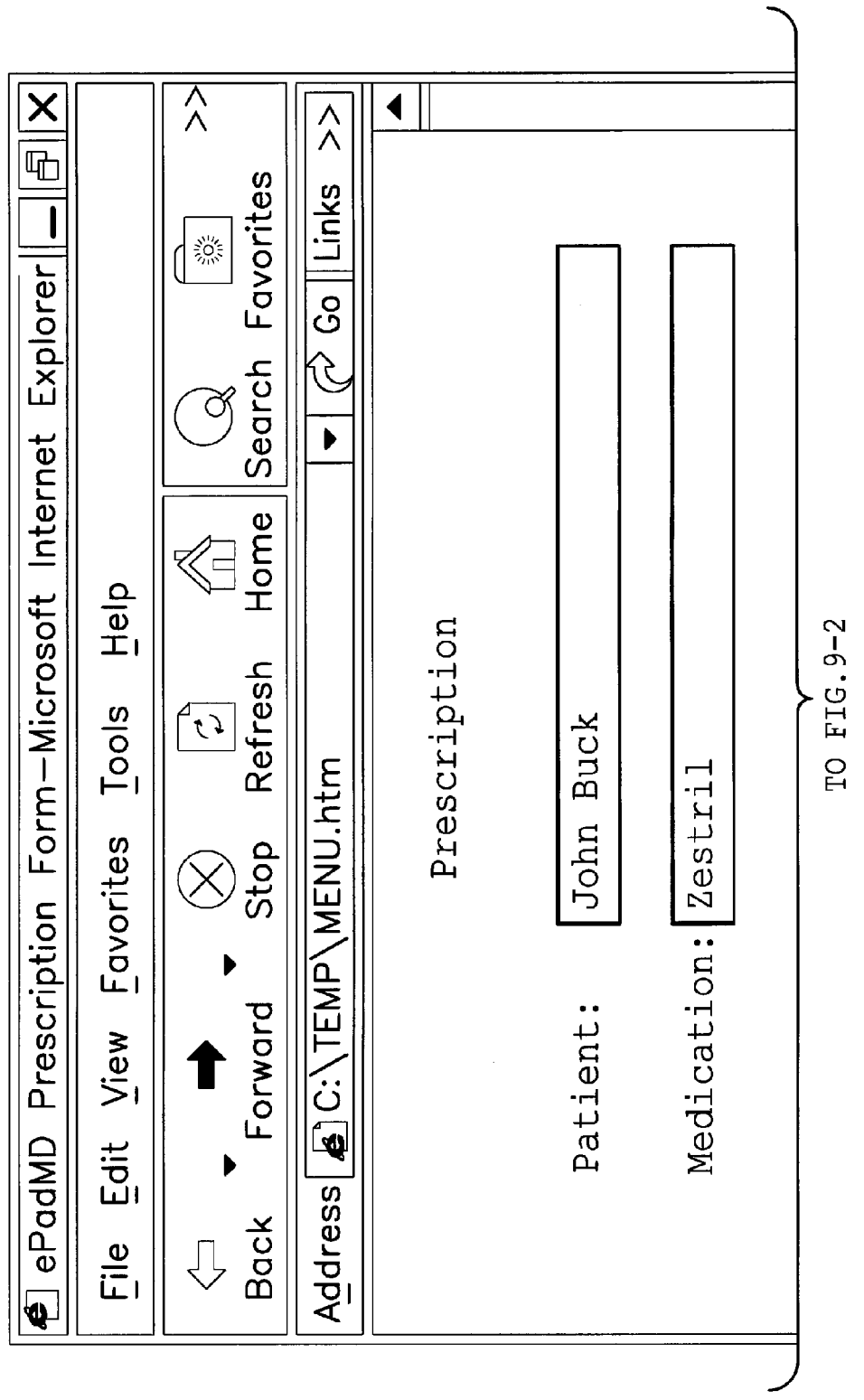
FIG. 9 is a screen shot showing a screen displaying prescription information for a prescription for Zestril, 10 mg, bid, in one embodiment of the invention.

In a preferred embodiment of the invention, the medication bar code is scanned and decoded, and the bar code reference number is used as key into a medication table that contains information used to construct a Web page containing a prescription information form for that medication. In certain embodiments of the invention the table is part of a database stored on the PDA. However, in a preferred embodiment the table is contained in a database stored on the server. For example, as shown in FIG. 2, table 209 forms part of prescription database 208 on server system 205. In certain embodiments of the invention the prescription information forms are stored as Web pages already including appropriate prescription information for each medication. In any case, as shown in FIG. 8, the system presents the prescriber with a form 801 including prescription information 802. Prescription information includes patient name, medication name, strength of the medication, dosage, quantity of medication to be dispensed (e.g., number of pills), and special instructions. As mentioned above, the bar code uniquely identifies both the medication name and strength (i.e., the number of milligrams of active ingredient per pill, tablet, or capsule). The form may also include information such as physician name and DEA number, physician phone and fax number, physician address, etc. FIG. 9 is a screen shot showing a screen displaying prescription information for a prescription for Zestril, 10 mg, bid, in one embodiment of the invention.

For most medications there is a particular dosage (e.g., once daily, twice daily, etc. depending upon the strength) that is appropriate for most patients. This most commonly selected dosage is chosen as the default value for dosage. For some drugs there is a standard quantity (e.g., number of pills) that is typically prescribed. For example, many antibiotics are to be taken for a specific number of days. For these medications, the default quantity will be selected to correspond with the appropriate quantity of medication. In other cases, for example for medications prescribed for chronic conditions such as hypertension, a convenient number such as 100 is selected as the default value. In some instances there may be special instructions, e.g., take at bedtime, take with food, that are usually part of the prescription information. These instructions are also displayed on the form. Of course if a patient has been given a prescription for a particular medication in the past, then the default values may be selected based on the previous prescription. Thus before displaying the form the server engine calls a routine to check whether the patient has previously received a prescription for the medication. If so, the parameters used in that prescription are displayed as default values.

Although default values are appropriate for many patients, there is a wide variety of permissible combinations of strength and dosage. An appropriate dose may range from a low dose that is therapeutically effective in a small subset of individuals to a maximum dose beyond which either no increases in efficacy are obtained or adverse effects become unacceptable. Therefore, in preferred embodiments of the invention in addition to displaying default values the form also displays other permissible strengths, dosages, and quantities.

Figure 10:
FIG. 10 is an image showing the use of drop-down lists for selection of alternate prescription information for Zestril.

In preferred embodiments of the invention these values are displayed on the PDA screen using a form-based approach, as shown, for example, in FIG. 10, which presents a prescription form for Zestril. As shown on this figure, various fields on the form are initially filled with default prescription information appropriate for Zestril. If the prescriber wishes to select these default values no editing of the fields is required. If the prescriber wishes to select an alternate value for a particular field, then as shown in FIG. 10, the prescriber can view alternate options on form 1001 by clicking on arrows 1002 for those fields. As shown on FIG. 10, the options can be provided as drop-down lists 1003 through which the prescriber can scroll. Alternatively, the options can be displayed as a vertical list with check boxes next to each item, in which the box next to the default option is checked. In some embodiments, for example if the list of options is too long to conveniently be displayed on the screen, the section of the screen containing the field can expand to fill a larger fraction of the screen, e.g., as described under the name of heirarchical data entry in U.S. Pat. No. 5,960,411, incorporated by reference above. In general, any display method that presents a default option and allows the user to rapidly select an alternative to the default option is suitable. If the prescriber accepts the default option no further action is needed. If the prescriber wishes to select a different option, he or she takes appropriate action such as using the stylus to select the corresponding button, using arrow keys to scroll down to the desired option, etc. For most information fields one of the options will be labeled "Other". If "Other" is selected, the user is prompted to enter a value or text input using the stylus and alphanumeric keyboard feature of the PDA or equivalent text entering system of a cellular phone. Thus the system provides for rapid and efficient entry of standard prescription information but allows flexibility for situations that differ from the norm. In a preferred embodiment of the invention the final step in creating the prescription is for the prescriber to provide his or her signature in field 1004. The signature is used in combination with the registration number to confirm that an authorized prescriber has created the prescription. As described above, digital signature technology is well known in the art.

In a particularly preferred embodiment of the invention, the form is presented as a Web page transmitted from the EpadMD Web server, and the prescription information is transmitted to the Web server by clicking a submit button. In a preferred embodiment of the invention the Web page is implemented using Microsoft's Active Server Pages (ASP), however a variety of other implementations are possible and are within the scope of the invention. In certain embodiments of the invention the forms are created by a form-based GUI (graphical user interface) application rather than using HTML forms. This application can be stored on the PDA or on a linked PC. Embodiments of the invention in which certain HTML documents (e.g., medication forms) are stored on the PDA or on a linked PC rather than being transmitted from the EpadMD Web service are within the scope of the invention.

In preferred embodiments of the invention the prescription information is entered while the prescriber's PDA is connected to the Internet either directly or via a PC. In this case the prescription entry forms are Web pages. In these embodiments the Web pages can offer links to databases containing, e.g., medication information such as package inserts, patient record information, etc. In certain embodiments of the invention patient records are accessible by the server engine, thus allowing updating of the patient record to reflect the fact that the prescription was written.

In any event, once the prescriber has selected the desired prescription information options, signed the prescription, and submitted the signed form to the EpadMD Web service as described below, the prescription is complete and is considered a created prescription.

Although the description above has focused on the entry of information using a form-based approach, the invention also encompasses the use of voice recognition software to allow the entry of any of the information discussed above and, in general, to issue instructions to perform any of the functions available to a user of the inventive system.

Information Transmission from PDA to EpadMD Web Service

Information is transmitted from the prescriber's PDA to the EpadMD Web service. In a preferred embodiment of the invention the information is transmitted via a PC located at the site where a prescription is generated. The PC is connected to the Internet via a digital subscriber line (DSL), integrated services digital network (ISDN), cable modem, analog modem, or any other available means. In a preferred embodiment of the invention the PDAs contain a wireless modem, and a wireless modem is also attached to the PC via a standard Ethernet network enabling the PDAs and PC to communicate in a wireless fashion. In this embodiment the PDAs in use at a particular site communicate with the EpadMD Web service via the PC, but in a fashion that is completely transparent to the PDA's users. The PC merely serves as a gateway between the Internet and a wireless network that links the PDAs in use at the site and the PC. Any available means can be used to link the PDAs with the PC. For example, the PDAs can be linked to the PC via LAN, wireless LAN, or bluetooth technology. Information is entered directly on a form using a browser installed on the PDA, and the form is submitted to the EpadMD Web service in the same way that forms are transmitted to Web servers from browsers installed on personal computers, i.e., using hypertext transfer protocol (HTTP). In certain embodiments of this implementation no data needs to be stored on the PC other than the software necessary to manage the modem and the Internet connection.

In another embodiment the PDA is periodically docked to a cradle connected to the PC and prescription information is uploaded to the PC at this time using synchronization technology mentioned above that is a standard feature of PDAs. The a particular embodiment of this approach, information is used to update a local prescription database stored on the PC. Each time a prescription is created an entry containing the prescription information is appended to a file (in essence, a transaction queue file) that is flagged as an upload file to be handled by the synchronization mechanism. When the PDA is cradled, the transaction queue file is uploaded to the PC and placed in a special directory reserved for transaction queue files. After completion of the upload the file is emptied to avoid duplicate transmissions. Update detection software on the PC periodically checks this directory for new files. When a new file is encountered, this application opens it, reads the entry, and inserts it into a table within a database on the PC. In a preferred embodiment of the invention Microsoft's SQL 7.0 database can be used. Each entry in the table is processed (e.g., by stored scripts associated with the database) and sent electronically to the EpadMD Web service, e.g., in the form of an e-mail message that would be created by message creation software on the PC and sent using a standard e-mail program. On the EpadMD Web server, e-mail processing software extracts the prescription information from the e-mail message and imports it into the prescription database. In another embodiment, messaging middleware such as the Microsoft Message Queuing (MSMQ) protocol is used to allow the Web server application to send and receive messages. MSMQ allows application programs to interact with one another by sending and receiving messages in a similar manner to that in which e-mail allows individuals to communicate with one another. However, creation and processing of the messages occurs automatically with no intervention from a user required. In a preferred version of this embodiment the database on the PC also includes a table that can receive confirmations or exceptions (e.g., indications of upload failure or missing information) from the Web server. In this case a user correction screen is displayed allowing correction of errors on the original prescription that prevented its acceptance by the EpadMD Web server.

In another embodiment that will likely assume greater importance in the future, the PDA contains a wireless digital modem that enables it to communicate directly over a cellular network as is currently possible with some PDAs such as the Palm VII. In this embodiment the PDA transmits prescription information directly to the EpadMD Web service without requiring a PC intermediary. The information may be sent in any of the ways described above, i.e. as a form using a Web browser on the PDA, as an e-mail message from the PDA to the Web service, or using a messaging protocol such as MSMQ.

Prescription Information Processing by the EpadMD Web Service

Once the prescription information for a created prescription is received by the EpadMD Web service, it is stored as a record in the prescription table. In addition, in a preferred embodiment of the invention bar code generating module X generates a reference number and corresponding bar code that are uniquely associated with the database record. Although in a preferred embodiment of the invention the bar code and reference number are generated by the EpadMD Web service, in certain embodiments of the invention software on the PDA or on a PC through which the PDA and the Web service communicate can generate the bar code and reference number. The reference number serves as a unique identifier of the prescription record and is stored in one of the record fields, serving as the key into the table. In other words, searching on a particular reference number retrieves the record associated with that reference number. As described below, upon completion of prescription information entry, a prescription ticket is printed at the location where the prescription was created. If a pharmacy was specified at the time the prescription was created, the EpadMD Web server transmits the created prescription to the pharmacy. Alternatively, a patient can access the EpadMD Web service via the Internet and select the desired pharmacy after the office encounter, at which time the EpadMD Web service transmits the prescription information to the pharmacy. Yet another embodiment enables the patient to phone the EpadMD Web service and select the desired pharmacy from a list presented by an automated attendant.

In another embodiment, the patient presents the ticket to a pharmacy that has not been specified in advance. In this embodiment the pharmacist accesses the EpadMD Web service to confirm the prescription as described above, fills the prescription, and indicates to the Web service that the prescription has been filled. The EpadMD Web service then updates the prescription database to reflect the fact that the prescription has been filled and also to indicate which pharmacy filled the prescription.

The invention permits the customer (e.g., the patient) to change his or her mind even after a particular pharmacy has been specified. The customer can access the EpadMD Web site and alter the pharmacy selection. The EpadMD Web service then transmits the prescription information to the newly selected pharmacy and, in certain embodiments of the invention, transmits a cancellation order to the pharmacy that was initially specified. However, it is not necessary for the customer to change the specified pharmacy. The customer is free to present the ticket at any pharmacy, regardless of whether that pharmacy or a different pharmacy or no pharmacy at all has been specified. A pharmacist working at any pharmacy can access the EpadMD Web site and, using the bar code on the ticket, perform prescription confirmation and fulfillment. In the event that the prescription is filled at a pharmacy other than the specified pharmacy, the EpadMD Web service transmits a cancellation order to the specified pharmacy.

(i) Printing Prescription Ticket

The EpadMD server engine sends a print job to a PC located at the site from which the prescription information was transmitted. This PC is attached to a printer via either a printer port or a local network such as Ethernet and sends the print job to the linked printer. The print job contains instructions to print a "ticket" containing the bar code and the created prescription including patient name, drug, dosage, etc. The paper ticket is given to the patient (e.g., during the patient checkout process) and serves as a "claim check" to be presented at the pharmacy where the patient will pick up the prescription. It is noted that in some embodiments of the invention printing of a "claim check" for presentation at the pharmacy is not a necessary feature. Since prescription information is transmitted directly to the pharmacy, in some embodiments of the invention the patient can present an appropriate identifier when picking up his or her prescription. Such identifier could be a driver's license or other photo ID or a card bearing some other form of identification such as fingerprint, biometric token, etc.

In a preferred embodiment of the invention the EpadMD Web service is configured to permit some flexibility regarding the identity of the individual picking up the prescription. For example, in the case of minor or persons with caretakers, the system is provided with a selection of individuals authorized to pick up the prescription.

(ii) Pharmacy Notification and Transmission of Prescription Information

To participate in the EpadMD system, a pharmacy must have a computer with Internet access, a browser, and a bar code scanner (e.g., a wedge scanner). The EpadMD server engine notifies the pharmacy specified in the prescription form that the prescription is to be fulfilled by transmitting a prescription fulfillment order to the pharmacy. Notification can take place in a variety of ways depending upon the hardware and software available at the pharmacy and the preference of the pharmacy. In a preferred embodiment of the invention the server engine sends an e-mail message to the pharmacy. The e-mail message is configured to auto print and/or cause the computer to beep upon arrival at the pharmacy computer. Alternatively, or in addition to the e-mail with auto print and/or beep, a pharmacist can be directly paged when a prescription fulfillment order is sent to the pharmacy. Paging can be accomplished, e.g., by sending an e-mail message to a Web-based paging service, which can be done automatically by the server. Instead of or in addition to sending an e-mail message to the pharmacy, the server can send a print job to a printer or fax machine attached to a computer at the pharmacy. In certain embodiments notification is done using XML-RPI. As is known in the art, XML-RPI is a specification and a set of implementations that allow software running on disparate operating systems, running in different environments to make procedure calls over the Internet. Thus XML-RPI allows remote procedure calling using HTTP as the transport and XML as the encoding. Although designed to be as simple as possible, XML-RPI allows complex data structures to be transmitted, processed and returned. In other embodiments Electronic Data Interchange (EDI), which is familiar to one of skill in the art, is used for notification. EDI is defined as "The electronic exchange of business documents (purchase orders, invoices, application forms, etc.) from one organization's computer to another organization's computer in standard data formats." EDI is based on a set of standard formats that define transaction sets (or messages) that can be used to send basic business data from one computer to another. These transaction sets replace paper documents such as purchase orders, invoices, and bills of lading. Additional information regarding EDI is found, e.g, at http://www.fms.treas.gov/edi and in the publication "Electronic Data Interchange Guidebook", U.S. Department of the Treasury, August, 1996, which is herein incorporated by reference. Other means and formats for notification are also within the scope of the invention.

The contents of the notification can vary but in all cases should be sufficient to allow the pharmacist to access the necessary information to fulfill the prescription. In preferred embodiments of the invention, the notification message contains all information needed for the pharmacist to fulfill the prescription, including patient name, medication name, strength, dosage, quantity, instructions, etc. Additional information such as billing information, insurance data and the like can also be provided. At a minimum, the notification could contain the reference number that is the content of the bar code generated for the prescription. The pharmacist could then access the EpadMD Web site and, after entering his or her PIN, would be presented with a Web page offering options including retrieval of prescription information. Upon selection of this option, a Web page requesting entry of a reference number is sent to the pharmacist. The pharmacist enters the reference number, which is used as a key into the prescription table. Prescription information is extracted and transmitted via a Web page back to the computer from which the request issued.

Although the description herein assumes that the pharmacy is a traditional pharmacy to which a patient would go to pick up his/her medication, this need not be the case. The pharmacy could send the medication to the patient. In addition, the EpadMD system can be integrated with currently existing or future "Internet pharmacies" such as PlanetRX (http://www.planetrx.com). Currently such pharmacies must receive either receive a copy of a prescription by mail or fax or the physician must communicate with the Internet pharmacy by phone. Thus, although patients can conveniently order prescription refills over the Internet, the initial process of transmitting the prescription information to the pharmacy remains inconvenient and vulnerable to fraud. If the patient's preferred pharmacy is an Internet pharmacy, the EpadMD Web service can notify the Internet pharmacy in any of the ways described above, e.g., e-mail, fax, etc. Thus the EpadMD Web service increases the ease of using Internet pharmacies and reduces the likelihood of fraud.

Prescription Fulfillment and Confirmation with the EpadMD System

In a preferred embodiment of the invention, as described above, the patient receives a paper ticket that contains the bar code and prescription information. The patient presents the ticket at a pharmacy. Since the pharmacist may have already been notified of the prescription by the EpadMD Web service (in the case that a pharmacy was selected when the prescription was created or at a later time), the medication may be ready by the time the customer arrives. However, in other cases the pharmacist dispenses the medication after the customer presents the prescription ticket.

(i) Medication Dispensing

Regardless of whether dispensing occurs before or after the patient presents the ticket, in certain embodiments of the invention, the pharmacist uses the EpadMD server engine to perform a checking procedure when dispensing the medication. In the case that the pharmacist dispenses the medication before the patient presents the ticket, in a preferred embodiment the pharmacist first accesses the EpadMD Web site. The pharmacist selects a "Dispense" option, and the server engine sends a Web page requesting the entry of a prescription bar code or reference number. The pharmacist scans in the prescription bar code from the printed copy of the prescription that was previously transmitted by the Web site or enters a reference number. The pharmacist also scans the NDC bar code from the pharmacy stock container. The EpadMD system uses the NDC bar code in comparison with the prescription information corresponding to the entered bar code or reference number to check that the pharmacist is dispensing the correct medication as follows. The system identifies the medication in the stock container by using the bar code scanned from the container to look up the corresponding medication in the medication table and compares this medication with the medication specified in the prescription information for that prescription. If they do not match, the system informs the pharmacist of an error and does not permit the dispensing activity to continue. For example, if the pharmacist chooses the wrong stock container, the EpadMD system will inform the pharmacist of the error and will not confirm that the correct medication has been dispensed. If the prescription information specifies that generic substitution is not permitted and the pharmacist attempts to dispense a generic equivalent, the EpadMD system will inform the pharmacist that a generic medication should not be dispensed and will not confirm that the correct medication has been dispensed. In certain embodiments of the invention, at the time of dispensing the pharmacist affixes a label to the medication bottle to be given to the patient. The label contains prescription information, preferably including the patient's name, medication name, and instructions to the patient. In addition, the label preferably contains a bar code that identifies the medication in the EpadMD medication database, e.g., the bar code corresponding to the prescription.

(ii) Medication Delivery

When the patient arrives to pick up the medication, in a preferred embodiment of the invention the pharmacist accesses the EpadMD Web server using an Internet-connected computer at the pharmacy. In response to an action by the pharmacist (e.g., clicking a button labeled "Fulfill", the server engine sends a Web page containing a form (prescription fulfillment form) that prompts the pharmacist to scan the bar code on the prescription ticket. As mentioned above, in certain embodiments of the invention the pharmacy PC has a wedge scanner so that the decoded bar code reference number is treated just like data entered via the keyboard. Regardless of the particular scanning, reading, and decoding technology employed, the bar code reference number is entered in the appropriate field in the prescription fulfillment form. The pharmacist then submits the form to the server. The server engine uses the bar code reference number to check the corresponding prescription information from the prescription table. In particular, the server engine checks the prescription status data. For example, if the prescription has already been fulfilled, this fact is reflected in the prescription status data as described below. Thus the EpadMD system can ensure that prescription tickets are not photocopied and used to obtain unauthorized medication. Also, if a PDA unit is lost, then prescriptions created by that unit after a specified time and date (e.g., time and date of loss or theft or best estimate) can be invalidated. If the server engine confirms the prescription (i.e., the prescription status data indicates that the prescription has not already been filled and/or there are refills remaining and the prescription has not been invalidated) it returns a Web page to display the prescription information in human-readable form. The pharmacist can then check to make sure that the information sent by the server engine matches that on the prescription ticket. If the pharmacist has already dispensed the medication (e.g., in the case that the pharmacy was previously notified of the prescription), the pharmacist then gives the medication to the patient. Optionally, a checking step can be performed in which a bar code on a label affixed to the medication container is scanned. The EpadMD system uses the bar code to confirm that the correct bottle is being given to the patient. If the pharmacist has not already dispensed the medication, then the pharmacist dispenses the medication as described above. When the pharmacist gives the medication to the patient, he or she sends the server engine an indication that the prescription has been picked up by the patient. For example, the Web page can contain a check box labeled "Prescription Filled". When the pharmacist checks this box and clicks the Submit button on this page, data indicating that the box is checked is sent to the server. In certain embodiments of the invention indication that the prescription has been fulfilled is provided simply by scanning the bar code on the prescription ticket. In any event, no matter how the pharmacist indicates that the prescription has been filled, the server engine updates the prescription table (e.g., the prescription status data stored in the table) to reflect the fact that the prescription has been filled. As mentioned above, in certain embodiments of the invention the patient does not need to present a paper ticket in order to pick up his or her prescription but can present appropriate ID such as a driver's license instead.

(iii) Interaction with Pharmacy Database Systems

Many pharmacies have their own data management systems used to track prescriptions, prices, inventory, and the like. Such systems frequently rely on bar codes to facilitate data access and management. For example, a bar code may be generated at the pharmacy for each prescription, with the bar code reference number serving as the key to a database record containing patient name, medication, strength, dosage, quantity, physician, billing information, lot or batch number information, etc. Such a database can be integrated with an inventory database, so that when a prescription is filled the inventory data (e.g., stock on hand) is updated. In certain preferred embodiments of the invention the EpadMD system can be integrated with individual pharmacy data management systems, e.g., for updating pharmacy inventory records when prescriptions are filled. In certain embodiments of the invention the EpadMD system prints out a label for application to the medication container to be given to the patient. In other embodiments of the invention, if the pharmacist uses the pharmacy's data management system to print a bar coded label for the prescription bottle, the EpadMD system can be used to scan the prescription label and confirm that the prescription label corresponds to the prescription as created by the prescriber.

In certain embodiments of the invention the EpadMD Web service interacts directly with a pharmacy data management system. For example, the EpadMD Web service can enter prescription information directly into the pharmacy database, thus allowing a single bar code and reference number to be used. With the growth of business-to-business communications via the Internet, the invention encompasses direct communication between the EpadMD Web service and pharmacy Web sites.

Notifications to Prescriber

As mentioned above, in a preferred embodiment of the invention after a prescription is filled the pharmacy transmits notification to the EpadMD Web server engine confirming that the prescription has been filled. In a particularly preferred embodiment of the invention, if the prescription has not been filled within a predetermined amount of time, the EpadMD server engine informs the prescriber of this fact so that the prescriber can contact the patient if necessary. In addition, in a particularly preferred embodiment each unit keeps track of when patients taking medications on a long term basis are close to running out of medication and alerts the prescriber so that the prescriber can contact the patient. In certain embodiments of the invention the patient is notified if he or she does not fill the prescription within a predetermined time or if the prescription is close to running out.

Sample Dispensing with the EpadMD System

From many perspectives, the dispensing of a sample by a physician to a patient is similar to the prescribing of a medication. Records of samples given to a patient must be kept for the purposes of maintaining an accurate medical record, requiring that the prescriber transcribe prescription information either into a written chart or enter it into a computerized medical record. The present invention facilitates the process of record keeping associated with sample dispensing while also providing a mechanism by which to track supplies of samples.

In certain embodiments of the invention, if a prescriber wishes to dispense a sample to a patient rather than selecting the "create prescription" option upon first accessing the EpadMD system, the prescriber selects the "dispense sample" option. The prescriber enters the patient identification information and medication identification information as described above. The medication identification information can be scanned directly from the sample package. The prescriber is prompted to enter the number of sample packets to be dispensed (a default value of 1 can be assumed). If the prescriber practices out of more than one location, as determined by checking the prescriber table, the system presents a screen listing the different locations and asking the prescriber to select the appropriate location. The system then displays a form containing prescription information corresponding to the medication and dosage unit indicated by the bar code, and creation of the prescription proceeds as described above. The prescription is entered into the prescription table just as though it was to be filled at a pharmacy. However, rather than transmitting the prescription information to a pharmacy, the EpadMD system instead updates the sample inventory table to reflect the fact that a sample from the sample stock at the prescriber's location has been used. In embodiments of the invention in which patient records are accessible by the server engine, the patient record can be updated as well.

The sample inventory table can be used by pharmaceutical sales representatives to keep track of the number of samples of any particular medication available at each location. In certain embodiments of the invention sales representatives are provided with PDAs and are able to view and update the sample inventory table for products that they represent. In other embodiments of the invention sales representatives update the sample inventory from a computer. In yet other embodiments the sample inventory table is updated by an employee or a computer system of a pharmaceutical company. In general, any type of client system, automated or manual, can be used to update the sample inventory table provided that the user has appropriate authorization.

In a preferred embodiment of the invention when a sales representative gives samples to a physician, the sales representative accesses the EpadMD Web site, which provides Web pages allowing the representative to enter the location, medication product bar code, and number of samples given. The sales representative or regional sales office can be automatically notified (e.g., by e-mail) when the sample stock of a particular product is running low at one of the locations for which he or she is responsible. The sales representative can also directly check the sample inventory table by accessing the EpadMD web service.

In certain embodiments of the invention the PDAs are location specific to facilitate recharging and compatibility with wireless technology available at the location. In this embodiment cookies can be used to register a PDA in one location at which prescriptions may be created and samples dispensed. Then location information would be obtained from the cookie by the Web server when location information is needed, e.g., when a sample is dispensed. The EpadMD system can proactively e-mail, fax, page, or communicate using any other available means with a sales representative when a particular sample supply is low and can provide reports of utilization history and feedback. Additionally, patients given samples can be asked to provide feedback, e.g., comments or evaluation of the medication, to the EpadMD Web service. Such information can be forwarded to the sales representatives or the pharmaceutical manufacturer.

Performing Market Research

The prescription table provides a useful source of information for purposes of market research. Since all prescriptions are recorded, and since the prescription table includes geographical and date information, the table can be used for a variety of purposes. At the present time there is no effective, integrated means of tracking prescriptions on a large scale, either at the level of prescription writing by the physician or prescription fulfillment by the pharmacy. The EpadMD system addresses this need. Using the information made available through the inventive system, prescribing trends can be monitored, and the effects of advertising campaigns, the introduction of a competing product, availability of a generic formulation, etc., can be assessed. The information is up-to-date and accurate and does not depend on unreliable and labor-intensive data-gathering instruments such as retrospective surveys.

Access to the prescription table can be provided on a subscription basis, e.g., to pharmaceutical companies, market research organizations, investment analysts, public interest research groups, government organizations, etc. The data can also be provided to various proprietary data providers.

In preferred embodiments of the invention, only a portion of the information in the prescription table is provided to a subscriber, the portion depending upon the identity of the subscriber. Different subscribers are permitted different degrees of access to the information based, for example, on the PIN used to access the information. For example, in preferred embodiments of the invention confidential information such as the name of a physician who prescribed a particular medication, the name of a patient for whom a medication was prescribed, etc., is not available for market research purposes. Furthermore, different pharmaceutical manufacturers may only be provided with information relevant to their own products rather than being permitted to view information relevant to competitors' products.

Security Considerations

In preferred embodiments of the invention information such as prescription information, patient and physician ID, etc., is transmitted between the prescriber's PDA, the EpadMD Web server, and the pharmacy in a secure fashion, preferably encrypted in accordance with current standards for secure Internet transactions. Such standards may be found, for example, in various publications known as Request For Comments (RFCs) made available under the auspices of the Internet Engineering Task Force (IETF) and accessible at the IETF Web site (http://www.ietf.org).

As described above, each user's access to the data stored by the EpadMD system will be based upon his or her PIN. Thus pharmaceutical sales representatives will not have access to patient information, and each prescriber will have access to information for his or her patients but not for other patients. Individuals performing market research will be granted access to information on their company's products but not to patient information or information about the products of other companies.

Further security measures include physically limiting access to the EpadMD server to only authorized individuals.

Additional Features

Although the description above focuses on the prescription creation features of the EpadMD Web service, a variety of other functions are provided in preferred embodiments of the invention. For example, in a preferred embodiment the inventive system offers in-house paging for physicians as well as a dictation service. These features are available through the PDAs and are coordinated by the inventive Web service using technology known to those skilled in the art. In addition, in preferred embodiments the system provides access a virtual medical record, that includes lab results, imaging results and reports, and other medical information such as history and physical, physician notes, etc. Data such as lab results can be entered directly into databases accessible to the EpadMD server engine either manually or automatically. Alternatively, the system can be configured to query or extract information from remote databases that may contain the information. In certain embodiments the invention also provides a link to the patient's insurance information. Prescribers may utilize the PDAs to access Continuing Medical Education offerings via the Internet. The inventive Web service can keep track of prescriber utilization of such offerings.

Other Embodiments

The EpadMD system as described above uses ID bar codes for both entering patient and medication ID and for identifying the information associated with each created prescription stored in the prescription database. However, in an alternative embodiment of the invention a 2D bar code (e.g., a PDF417 format bar code) is used to encode the information for each created prescription. In this embodiment, rather than extracting the prescription information from the database to be sent to the pharmacy or requiring that the pharmacist access the prescription database to retrieve the data needed to fill a prescription, the EpadMD Web service simply sends a 2D bar code encoding the prescription information to the pharmacy. The pharmacist uses a scanner capable of reading 2D bar codes to read the prescription information, or a computer equipped with software to decode 2D bar codes issues a request to a printer at the pharmacy to print the prescription in human-readable format.

The use of 2D bar codes simplifies transmission of prescription information since it eliminates a step of database lookup. However, in a preferred embodiment of the 2D implementation, prescription information for created prescriptions is stored in non-bar-coded format for aspects of the invention such as performing market research, sample tracking, and validating prescriptions.

What is claimed is:

1. A server system for interactively creating and managing prescriptions comprising:

a data storage medium configured to store information for a plurality of prescribers and medications;

a prescription creation component embodied on computer-readable medium configured to receive prescription information that is contained in a bar code scanned by a prescriber from one of a plurality of bar code sources, which prescription information includes medication identification information comprising at least one of: a medication name, a medication identification number, and a bar code assigned to the medication;

a prescription form component embodied on a computer-readable medium configured to:

i) retrieve information from the data storage medium based on the scanned bar code; ii) present to the prescriber a plurality of options for at least one element of prescription information; iii) receive from the prescriber selection input selecting among the presented plurality of options for at least one element of prescription information; and iv) generate or selects a prescription form responsive to the medication identification information and the selection input;

a prescription database record generated responsive to the received selection input and the medication identification information; and a prescription management interface configured to:

receive from a first nonprescriber user, via a prescription fulfillment system a) an identification of a generated prescription; and b) a request for modification of the prescription database record;

receive a) authorization information, and b) a request for a modification of the prescription database record from a second nonprescriber user in at least one of a plurality of categories of nonprescriber users, the plurality of categories of nonprescriber users including at least one of: pharmacy employees, sales representatives, pharmaceutical company employees, patients, and market researchers; and transmit to a server engine requests for modification received from one or more nonprescriber users; and the server engine configured to modify the prescription database record responsive to the requests for modification received from the prescription management interface.

2. The server system of claim 1, wherein the information for each of a plurality of medications includes a bar code, bar code reference number, or bar code character string.

3. The server system of claim 1, wherein the prescription form comprises at least one Web page.

4. The server system of claim 1, wherein the data storage medium further stores information for a plurality of patients.

5. The server system of claim 4, wherein the information for each of a plurality of patients includes a bar code, bar code reference number, or bar code character string.

6. The server system of claim 1, wherein the data storage medium further stores information for a plurality of pharmacies.

7. The server system of claim 1, wherein the data storage medium further stores information for a plurality of created prescriptions.

8. The server system of claim 1, further comprising a bar code generating component.

9. The server system of claim 1, further comprising a prescription creation component that processes data received from prescribers and stores prescription information for a plurality of prescriptions in the data storage medium.

10. The server system of claim 7 or claim 9, wherein the information for each of a plurality of created prescriptions includes a bar code or bar code reference number or bar code character string.

11. The server system of claim 1, further comprising a prescription maintenance component that updates prescription information and prescription status data in response to information received from a client system.

12. The server system of claim 1, further comprising an access control component that receives identification information from a plurality of users and uses the information to allow or prevent users from viewing or changing data stored in the data storage medium.

13. The server system of claim 1, wherein the prescription management interface further comprises an interface for receiving, from a patient, a request for a modification of an identification of a preferred prescription fulfillment system.

14. The server system of claim 1, wherein the prescription management interface further comprises an interface for receiving, from a market researcher, a request for access to prescription fulfillment data associated with the prescription database record.

15. The server system of claim 1, wherein the prescription management interface further comprises an interface for receiving, from a sales representative, a request for access to prescription fulfillment data associated with the prescription database record.

16. The server system of claim 1, wherein the prescription management interface further comprises an interface for receiving, from an employee of a pharmaceutical company, a request for access to prescription fulfillment data associated with the prescription database record and associated with a prescription drug distributed by the pharmaceutical company.

* * * * *